(12) United States Patent
Tamiz et al.

(10) Patent No.: US 8,198,233 B2
(45) Date of Patent: Jun. 12, 2012

(54) SYNTHETIC PEPTIDES THAT ENHANCE TIGHT JUNCTION PERMEABILITY

(75) Inventors: Amir Tamiz, Silver Spring, MD (US); Min Lin, Forest Park, IL (US)

(73) Assignee: Alba Therapeutics Corporation, Baltimore, MD (US)

( * ) Notice: Subject to any disclaimer, the term of this patent is extended or adjusted under 35 U.S.C. 154(b) by 0 days.

(21) Appl. No.: 12/670,800

(22) PCT Filed: Jul. 28, 2008

(86) PCT No.: PCT/US2008/071321
§ 371 (c)(1),
(2), (4) Date: Jul. 28, 2010

(87) PCT Pub. No.: WO2009/015382
PCT Pub. Date: Jan. 29, 2009

(65) Prior Publication Data
US 2010/0286036 A1    Nov. 11, 2010

Related U.S. Application Data

(60) Provisional application No. 60/952,144, filed on Jul. 26, 2007, provisional application No. 60/953,398, filed on Aug. 1, 2007, provisional application No. 60/953,403, filed on Aug. 1, 2007, provisional application No. 60/953,405, filed on Aug. 1, 2007, provisional application No. 60/977,242, filed on Oct. 3, 2007.

(51) Int. Cl.
*A61K 38/00* (2006.01)
*A61K 31/01* (2006.01)

(52) U.S. Cl. .......................... 514/1.1; 530/300

(58) Field of Classification Search .................. None
See application file for complete search history.

(56) References Cited

U.S. PATENT DOCUMENTS

| 6,458,925 B1 * | 10/2002 | Fasano .......................... 530/328 |
| 2005/0266421 A1 | 12/2005 | Bird et al. |
| 2006/0276403 A1 | 12/2006 | Fasano et al. |

OTHER PUBLICATIONS

Berezowska et al., Dicarba Analogues of the Cyclic Enkephalin Peptides H-Tyr-c[DCys-Gly-Phe-D(orL)-Cys]NH2 Retain High Opioid Activity:, J. Med Chem., Mar. 22, 2007, vol. 50(6), pp. 1414-1417.
International Search Report issued in Intl. Appl. No. PCT/US08/71321 on Mar. 2, 2009, 5 pages.

* cited by examiner

*Primary Examiner* — Gyan Chandra
(74) *Attorney, Agent, or Firm* — Cooley LLP

(57) ABSTRACT

The present invention provides novel peptides that facilitate the opening of mammalian tight junctions, i.e. tight junction agonists. The present invention also provides methods for the treatment of disease by administering to a subject suffering from the disease a composition comprising a peptide tight junction agonist of the invention in combination with a therapeutically effective amount of an active agent.

6 Claims, 11 Drawing Sheets

Phe-AllylGly-Ile-Gly-Arg-Leu induces ZO-1 redistribution in Caco-2 BBE cells

FIGURE 11

```
                        SEQUENCE LISTING

<160> NUMBER OF SEQ ID NOS: 274

<210> SEQ ID NO 1
<211> LENGTH: 6
<212> TYPE: PRT
<213> ORGANISM: Unknown
<220> FEATURE:
<223> OTHER INFORMATION: Peptide tight junction agonist

<400> SEQUENCE: 1

Phe Cys Ile Gly Arg Leu
1               5

<210> SEQ ID NO 2
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -OH moiety

<400> SEQUENCE: 2

Phe Xaa Ile Gly Arg Leu
1               5

<210> SEQ ID NO 3
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 3

Phe Xaa Ile Gly Arg
1               5

<210> SEQ ID NO 4
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is D-allylglycine
<220> FEATURE:
<221> NAME/KEY: misc_feature
<222> LOCATION: (5)..(5)
<223> OTHER INFORMATION: Arg is modified with a C terminal -NH2 moiety
```

```
<400> SEQUENCE: 4

Phe Xaa Ile Gly Arg
1               5

<210> SEQ ID NO 5
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 5

Met Xaa Ile Gly Arg Leu
1               5

<210> SEQ ID NO 6
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 6

Gln Xaa Ile Gly Arg Leu
1               5

<210> SEQ ID NO 7
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 7

Leu Xaa Ile Gly Arg Leu
1               5

<210> SEQ ID NO 8
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
```

```
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 8

Ser Xaa Ile Gly Arg Leu
1               5

<210> SEQ ID NO 9
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 9

Thr Xaa Ile Gly Arg Leu
1               5

<210> SEQ ID NO 10
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 10

Glu Xaa Ile Gly Arg Leu
1               5

<210> SEQ ID NO 11
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 11

Val Xaa Ile Gly Arg Leu
1               5

<210> SEQ ID NO 12
<211> LENGTH: 6
<212> TYPE: PRT
<213> ORGANISM: Unknown
<220> FEATURE:
<223> OTHER INFORMATION: Peptide tight junction agonist
```

```
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 12

Tyr Xaa Ile Gly Arg Leu
1               5

<210> SEQ ID NO 13
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 13

Gly Xaa Ile Gly Arg Leu
1               5

<210> SEQ ID NO 14
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 14

Asp Xaa Ile Gly Arg Leu
1               5

<210> SEQ ID NO 15
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 15

Trp Xaa Ile Gly Arg Leu
1               5

<210> SEQ ID NO 16
<211> LENGTH: 6
```

```
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 16

Lys Xaa Ile Gly Arg Leu
1               5

<210> SEQ ID NO 17
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 17

Ala Xaa Ile Gly Arg Leu
1               5

<210> SEQ ID NO 18
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 18

His Xaa Ile Gly Arg Leu
1               5

<210> SEQ ID NO 19
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 19

Pro Xaa Ile Gly Arg Leu
1               5
```

```
<210> SEQ ID NO 20
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 20

Arg Xaa Ile Gly Arg Leu
1               5

<210> SEQ ID NO 21
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 21

Ile Xaa Ile Gly Arg Leu
1               5

<210> SEQ ID NO 22
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 22

Phe Xaa Pro Gly Arg Leu
1               5

<210> SEQ ID NO 23
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety
```

-continued

```
<400> SEQUENCE: 23

Phe Xaa Phe Gly Arg Leu
1               5

<210> SEQ ID NO 24
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 24

Phe Xaa Thr Gly Arg Leu
1               5

<210> SEQ ID NO 25
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 25

Phe Xaa Leu Gly Arg Leu
1               5

<210> SEQ ID NO 26
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 26

Phe Xaa Ser Gly Arg Leu
1               5

<210> SEQ ID NO 27
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
```

```
<221> NAME/KEY: misc_feature
<222> LOCATION: (6)..(6)
<223> OTHER INFORMATION: Leu is modified with a C terminal -NH2 moiety

<400> SEQUENCE: 27

Phe Xaa Phe Gly Arg Leu
1               5

<210> SEQ ID NO 28
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 28

Phe Xaa Val Gly Arg Leu
1               5

<210> SEQ ID NO 29
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 29

Phe Xaa Gly Gly Arg Leu
1               5

<210> SEQ ID NO 30
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 30

Phe Xaa Ala Gly Arg Leu
1               5

<210> SEQ ID NO 31
<211> LENGTH: 6
<212> TYPE: PRT
<213> ORGANISM: Unknown
<220> FEATURE:
<223> OTHER INFORMATION: Peptide tight junction agonist
<220> FEATURE:
```

```
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 31

Phe Xaa His Gly Arg Leu
1               5

<210> SEQ ID NO 32
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 32

Phe Xaa Asp Gly Arg Leu
1               5

<210> SEQ ID NO 33
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 33

Phe Xaa Glu Gly Arg Leu
1               5

<210> SEQ ID NO 34
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 34

Phe Xaa Gln Gly Arg Leu
1               5

<210> SEQ ID NO 35
<211> LENGTH: 6
<212> TYPE: PRT
```

```
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 35

Phe Xaa Arg Gly Arg Leu
1               5

<210> SEQ ID NO 36
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 36

Phe Xaa Lys Gly Arg Leu
1               5

<210> SEQ ID NO 37
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 37

Phe Xaa Asn Gly Arg Leu
1               5

<210> SEQ ID NO 38
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 38

Phe Xaa Tyr Gly Arg Leu
1               5
```

```
<210> SEQ ID NO 39
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 39

Phe Xaa Ile Thr Arg Leu
1               5

<210> SEQ ID NO 40
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 40

Phe Xaa Ile Leu Arg Leu
1               5

<210> SEQ ID NO 41
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 41

Phe Xaa Ile Ile Arg Leu
1               5

<210> SEQ ID NO 42
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 42
```

```
Phe Xaa Ile Ala Arg Leu
1               5

<210> SEQ ID NO 43
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 43

Phe Xaa Ile Pro Arg Leu
1               5

<210> SEQ ID NO 44
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 44

Phe Xaa Ile Gly Arg Leu
1               5

<210> SEQ ID NO 45
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 45

Phe Xaa Ile His Arg Leu
1               5

<210> SEQ ID NO 46
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
```

```
<222> LOCATION: (6)..(6)
<223> OTHER INFORMATION: Leu is modified with a C terminal -NH2 moiety

<400> SEQUENCE: 46

Phe Xaa Ile Asp Arg Leu
1               5

<210> SEQ ID NO 47
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 47

Phe Xaa Ile Glu Arg Leu
1               5

<210> SEQ ID NO 48
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 48

Phe Xaa Ile Gln Arg Leu
1               5

<210> SEQ ID NO 49
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 49

Phe Xaa Ile Phe Arg Leu
1               5

<210> SEQ ID NO 50
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
```

-continued

```
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 50

Phe Xaa Ile Arg Arg Leu
1               5

<210> SEQ ID NO 51
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 51

Phe Xaa Ile Lys Arg Leu
1               5

<210> SEQ ID NO 52
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 52

Phe Xaa Ile Asn Arg Leu
1               5

<210> SEQ ID NO 53
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 53

Phe Xaa Ile Ser Arg Leu
1               5

<210> SEQ ID NO 54
<211> LENGTH: 6
<212> TYPE: PRT
<213> ORGANISM: Unknown
```

```
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 54

Phe Xaa Ile Val Arg Leu
1               5

<210> SEQ ID NO 55
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 55

Phe Xaa Ile Gly His Leu
1               5

<210> SEQ ID NO 56
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 56

Phe Xaa Ile Gly Asp Leu
1               5

<210> SEQ ID NO 57
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 57

Phe Xaa Ile Gly Glu Leu
1               5
```

```
<210> SEQ ID NO 58
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 58

Phe Xaa Ile Gly Gln Leu
1               5

<210> SEQ ID NO 59
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 59

Phe Xaa Ile Gly Gly Leu
1               5

<210> SEQ ID NO 60
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 60

Phe Xaa Ile Gly Ala Leu
1               5

<210> SEQ ID NO 61
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 61
```

```
Phe Xaa Ile Gly Phe Leu
1               5

<210> SEQ ID NO 62
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 62

Phe Xaa Ile Gly Lys Leu
1               5

<210> SEQ ID NO 63
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 63

Phe Xaa Ile Gly Leu Leu
1               5

<210> SEQ ID NO 64
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 64

Phe Xaa Ile Gly Met Leu
1               5

<210> SEQ ID NO 65
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
```

```
<223> OTHER INFORMATION: Leu is modified with a C terminal -NH2 moiety

<400> SEQUENCE: 65

Phe Xaa Ile Gly Asn Leu
1               5

<210> SEQ ID NO 66
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 66

Phe Xaa Ile Gly Ser Leu
1               5

<210> SEQ ID NO 67
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 67

Phe Xaa Ile Gly Tyr Leu
1               5

<210> SEQ ID NO 68
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 68

Phe Xaa Ile Gly Thr Leu
1               5

<210> SEQ ID NO 69
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
```

<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 69

Phe Xaa Ile Gly Ile Leu
1               5

<210> SEQ ID NO 70
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 70

Phe Xaa Ile Gly Trp Leu
1               5

<210> SEQ ID NO 71
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 71

Phe Xaa Ile Gly Pro Leu
1               5

<210> SEQ ID NO 72
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 72

Phe Xaa Ile Gly Val Leu
1               5

<210> SEQ ID NO 73
<211> LENGTH: 6
<212> TYPE: PRT
<213> ORGANISM: Unknown
<220> FEATURE:

```
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: His is modified with a C terminal -NH2 moiety

<400> SEQUENCE: 73

Phe Xaa Ile Gly Arg His
1               5

<210> SEQ ID NO 74
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Asp is modified with a C terminal -NH2 moiety

<400> SEQUENCE: 74

Phe Xaa Ile Gly Arg Asp
1               5

<210> SEQ ID NO 75
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Arg is modified with a C terminal -NH2 moiety

<400> SEQUENCE: 75

Phe Xaa Ile Gly Arg Arg
1               5

<210> SEQ ID NO 76
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Phe is modified with a C terminal -NH2 moiety

<400> SEQUENCE: 76

Phe Xaa Ile Gly Arg Phe
1               5

<210> SEQ ID NO 77
```

```
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Ala is modified with a C terminal -NH2 moiety

<400> SEQUENCE: 77

Phe Xaa Ile Gly Arg Ala
1               5

<210> SEQ ID NO 78
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Gly is modified with a C terminal -NH2 moiety

<400> SEQUENCE: 78

Phe Xaa Ile Gly Arg Gly
1               5

<210> SEQ ID NO 79
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Gln is modified with a C terminal -NH2 moiety

<400> SEQUENCE: 79

Phe Xaa Ile Gly Arg Gln
1               5

<210> SEQ ID NO 80
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Glu is modified with a C terminal -NH2 moiety

<400> SEQUENCE: 80

Phe Xaa Ile Gly Arg Glu
```

-continued

```
<210> SEQ ID NO 81
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Thr is modified with a C terminal -NH2 moiety

<400> SEQUENCE: 81

Phe Xaa Ile Gly Arg Thr
1               5

<210> SEQ ID NO 82
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Tyr is modified with a C terminal -NH2 moiety

<400> SEQUENCE: 82

Phe Xaa Ile Gly Arg Tyr
1               5

<210> SEQ ID NO 83
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Ser is modified with a C terminal -NH2 moiety

<400> SEQUENCE: 83

Phe Xaa Ile Gly Arg Ser
1               5

<210> SEQ ID NO 84
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Asn is modified with a C terminal -NH2 moiety
```

```
<400> SEQUENCE: 84

Phe Xaa Ile Gly Arg Asn
1               5

<210> SEQ ID NO 85
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Met is modified with a C terminal -NH2 moiety

<400> SEQUENCE: 85

Phe Xaa Ile Gly Arg Met
1               5

<210> SEQ ID NO 86
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Lys is modified with a C terminal -NH2 moiety

<400> SEQUENCE: 86

Phe Xaa Ile Gly Arg Lys
1               5

<210> SEQ ID NO 87
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Ile is modified with a C terminal -NH2 moiety

<400> SEQUENCE: 87

Phe Xaa Ile Gly Arg Ile
1               5

<210> SEQ ID NO 88
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
```

```
<220> FEATURE:
<221> NAME/KEY: misc_feature
<222> LOCATION: (6)..(6)
<223> OTHER INFORMATION: Trp is modified with a C terminal -NH2 moiety

<400> SEQUENCE: 88

Phe Xaa Ile Gly Arg Trp
1               5

<210> SEQ ID NO 89
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Pro is modified with a C terminal -NH2 moiety

<400> SEQUENCE: 89

Phe Xaa Ile Gly Arg Pro
1               5

<210> SEQ ID NO 90
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is allylglycine
<220> FEATURE:
<221> NAME/KEY: misc_feature
<222> LOCATION: (6)..(6)
<223> OTHER INFORMATION: Val is modified with a C terminal -NH2 moiety

<400> SEQUENCE: 90

Phe Xaa Ile Gly Arg Val
1               5

<210> SEQ ID NO 91
<211> LENGTH: 6
<212> TYPE: PRT
<213> ORGANISM: Unknown
<220> FEATURE:
<223> OTHER INFORMATION: Peptide tight junction agonist

<400> SEQUENCE: 91

Phe Cys Ile Gly Arg Leu
1               5

<210> SEQ ID NO 92
<211> LENGTH: 6
<212> TYPE: PRT
<213> ORGANISM: Unknown
<220> FEATURE:
<223> OTHER INFORMATION: Peptide tight junction agonist

<400> SEQUENCE: 92

Phe Thr Ile Gly Arg Leu
1               5

<210> SEQ ID NO 93
```

```
<211> LENGTH: 6
<212> TYPE: PRT
<213> ORGANISM: Unknown
<220> FEATURE:
<223> OTHER INFORMATION: Peptide tight junction agonist

<400> SEQUENCE: 93

Phe Ser Ile Gly Arg Leu
1               5

<210> SEQ ID NO 94
<211> LENGTH: 6
<212> TYPE: PRT
<213> ORGANISM: Unknown
<220> FEATURE:
<223> OTHER INFORMATION: Peptide tight junction agonist

<400> SEQUENCE: 94

Phe Met Ile Gly Arg Leu
1               5

<210> SEQ ID NO 95
<211> LENGTH: 6
<212> TYPE: PRT
<213> ORGANISM: Unknown
<220> FEATURE:
<221> NAME/KEY: misc_feature
<222> LOCATION: (6)..(6)
<223> OTHER INFORMATION: Leu is modified with a C terminal -NH2 moiety
<220> FEATURE:
<223> OTHER INFORMATION: Peptide tight junction agonist

<400> SEQUENCE: 95

Phe Leu Ile Gly Arg Leu
1               5

<210> SEQ ID NO 96
<211> LENGTH: 7
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (7)..(7)
<223> OTHER INFORMATION: Leu is modified with a C terminal -NH2 moiety

<400> SEQUENCE: 96

Phe Phe Leu Ile Gly Arg Leu
1               5

<210> SEQ ID NO 97
<211> LENGTH: 6
<212> TYPE: PRT
<213> ORGANISM: Unknown
<220> FEATURE:
<223> OTHER INFORMATION: Peptide tight junction agonist

<400> SEQUENCE: 97

Phe Phe Ile Gly Arg Leu
1               5

<210> SEQ ID NO 98
<211> LENGTH: 6
<212> TYPE: PRT
<213> ORGANISM: Unknown
<220> FEATURE:
<223> OTHER INFORMATION: Peptide tight junction agonist

<400> SEQUENCE: 98
```

Phe Pro Ile Gly Arg Leu
1               5

<210> SEQ ID NO 99
<211> LENGTH: 6
<212> TYPE: PRT
<213> ORGANISM: Unknown
<220> FEATURE:
<223> OTHER INFORMATION: Peptide tight junction agonist

<400> SEQUENCE: 99

Phe Trp Ile Gly Arg Leu
1               5

<210> SEQ ID NO 100
<211> LENGTH: 6
<212> TYPE: PRT
<213> ORGANISM: Unknown
<220> FEATURE:
<223> OTHER INFORMATION: Peptide tight junction agonist

<400> SEQUENCE: 100

Phe His Ile Gly Arg Leu
1               5

<210> SEQ ID NO 101
<211> LENGTH: 6
<212> TYPE: PRT
<213> ORGANISM: Unknown
<220> FEATURE:
<223> OTHER INFORMATION: Peptide tight junction agonist

<400> SEQUENCE: 101

Phe Pro Ile Gly Arg Leu
1               5

<210> SEQ ID NO 102
<211> LENGTH: 6
<212> TYPE: PRT
<213> ORGANISM: Unknown
<220> FEATURE:
<223> OTHER INFORMATION: Peptide tight junction agonist

<400> SEQUENCE: 102

Phe Asp Ile Gly Arg Leu
1               5

<210> SEQ ID NO 103
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 103

Phe Leu Ile Gly Arg Leu
1               5

<210> SEQ ID NO 104
<211> LENGTH: 6
<212> TYPE: PRT
<213> ORGANISM: Unknown
<220> FEATURE:
<223> OTHER INFORMATION: Peptide tight junction agonist

```
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 104

Phe Phe Ile Gly Arg Leu
1               5

<210> SEQ ID NO 105
<211> LENGTH: 6
<212> TYPE: PRT
<213> ORGANISM: Unknown
<220> FEATURE:
<223> OTHER INFORMATION: Peptide tight junction agonist

<400> SEQUENCE: 105

Phe Arg Ile Gly Arg Leu
1               5

<210> SEQ ID NO 106
<211> LENGTH: 6
<212> TYPE: PRT
<213> ORGANISM: Unknown
<220> FEATURE:
<223> OTHER INFORMATION: Peptide tight junction agonist

<400> SEQUENCE: 106

Phe Gly Ile Gly Arg Leu
1               5

<210> SEQ ID NO 107
<211> LENGTH: 6
<212> TYPE: PRT
<213> ORGANISM: Unknown
<220> FEATURE:
<223> OTHER INFORMATION: Peptide tight junction agonist

<400> SEQUENCE: 107

Phe Gln Ile Gly Arg Leu
1               5

<210> SEQ ID NO 108
<211> LENGTH: 6
<212> TYPE: PRT
<213> ORGANISM: Unknown
<220> FEATURE:
<223> OTHER INFORMATION: Peptide tight junction agonist

<400> SEQUENCE: 108

Phe Glu Ile Gly Arg Leu
1               5

<210> SEQ ID NO 109
<211> LENGTH: 6
<212> TYPE: PRT
<213> ORGANISM: Unknown
<220> FEATURE:
<223> OTHER INFORMATION: Peptide tight junction agonist

<400> SEQUENCE: 109

Phe Lys Ile Gly Arg Leu
1               5

<210> SEQ ID NO 110
<211> LENGTH: 6
<212> TYPE: PRT
<213> ORGANISM: Unknown
```

```
<220> FEATURE:
<223> OTHER INFORMATION: Peptide tight junction agonist

<400> SEQUENCE: 110

Phe Asn Ile Gly Arg Leu
1               5

<210> SEQ ID NO 111
<211> LENGTH: 6
<212> TYPE: PRT
<213> ORGANISM: Unknown
<220> FEATURE:
<223> OTHER INFORMATION: Peptide tight junction agonist

<400> SEQUENCE: 111

Phe Tyr Ile Gly Arg Leu
1               5

<210> SEQ ID NO 112
<211> LENGTH: 6
<212> TYPE: PRT
<213> ORGANISM: Unknown
<220> FEATURE:
<223> OTHER INFORMATION: Peptide tight junction agonist

<400> SEQUENCE: 112

Phe Leu Ile Gly Arg Leu
1               5

<210> SEQ ID NO 113
<211> LENGTH: 6
<212> TYPE: PRT
<213> ORGANISM: Unknown
<220> FEATURE:
<223> OTHER INFORMATION: Peptide tight junction agonist

<400> SEQUENCE: 113

Phe Val Ile Gly Arg Leu
1               5

<210> SEQ ID NO 114
<211> LENGTH: 6
<212> TYPE: PRT
<213> ORGANISM: Unknown
<220> FEATURE:
<223> OTHER INFORMATION: Peptide tight junction agonist

<400> SEQUENCE: 114

Phe Ile Ile Gly Arg Leu
1               5

<210> SEQ ID NO 115
<211> LENGTH: 6
<212> TYPE: PRT
<213> ORGANISM: Unknown
<220> FEATURE:
<223> OTHER INFORMATION: Peptide tight junction agonist

<400> SEQUENCE: 115

Ser Leu Ile Gly Arg Leu
1               5

<210> SEQ ID NO 116
<211> LENGTH: 6
<212> TYPE: PRT
<213> ORGANISM: Unknown
<220> FEATURE:
<223> OTHER INFORMATION: Peptide tight junction agonist
```

```
<220> FEATURE:
<221> NAME/KEY: misc_feature
<222> LOCATION: (6)..(6)
<223> OTHER INFORMATION: Phe is modified with a C terminal -NH2 moiety

<400> SEQUENCE: 116

Leu Arg Gly Ile Leu Phe
1               5

<210> SEQ ID NO 117
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 117

Phe Leu Ile Gly Arg
1               5

<210> SEQ ID NO 118
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-beta-(2-thienyl)-alanine

<400> SEQUENCE: 118

Phe Xaa Ile Gly Arg Leu
1               5

<210> SEQ ID NO 119
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Homoserine

<400> SEQUENCE: 119

Phe Xaa Ile Gly Arg Leu
1               5

<210> SEQ ID NO 120
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-alpha-aminobutyric acid

<400> SEQUENCE: 120

Phe Xaa Ile Gly Arg Leu
1               5

<210> SEQ ID NO 121
```

```
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-methionine-sulfoxide

<400> SEQUENCE: 121

Phe Xaa Ile Gly Arg Leu
1               5

<210> SEQ ID NO 122
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-methionine-sulfone

<400> SEQUENCE: 122

Phe Xaa Ile Gly Arg Leu
1               5

<210> SEQ ID NO 123
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Cys

<400> SEQUENCE: 123

Phe Cys Ile Gly Arg Leu
1               5

<210> SEQ ID NO 124
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Norvaline

<400> SEQUENCE: 124

Phe Xaa Ile Gly Arg Leu
1               5

<210> SEQ ID NO 125
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-norleucine

<400> SEQUENCE: 125
```

```
Phe Xaa Ile Gly Arg Leu
1               5

<210> SEQ ID NO 126
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated
<220> FEATURE:
<221> NAME/KEY: misc_feature
<222> LOCATION: (2)..(2)
<223> OTHER INFORMATION: Xaa is Homoserine

<400> SEQUENCE: 126

Phe Xaa Ile Gly Arg Ala
1               5

<210> SEQ ID NO 127
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated
<220> FEATURE:
<221> NAME/KEY: misc_feature
<222> LOCATION: (2)..(2)
<223> OTHER INFORMATION: Xaa is Homoserine

<400> SEQUENCE: 127

Phe Xaa Ile Gly Arg Ser
1               5

<210> SEQ ID NO 128
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated
<220> FEATURE:
<221> NAME/KEY: misc_feature
<222> LOCATION: (2)..(2)
<223> OTHER INFORMATION: Xaa is Homoserine

<400> SEQUENCE: 128

Phe Xaa Ile Gly Arg Phe
1               5

<210> SEQ ID NO 129
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Homoserine

<400> SEQUENCE: 129
```

```
Phe Xaa Ile Gly Arg Phe
1               5

<210> SEQ ID NO 130
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-S-benzyl-cysteine

<400> SEQUENCE: 130

Phe Xaa Ile Gly Arg Leu
1               5

<210> SEQ ID NO 131
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-S-tert-butylthio-cysteine

<400> SEQUENCE: 131

Phe Xaa Ile Gly Arg Leu
1               5

<210> SEQ ID NO 132
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-phenylglycine

<400> SEQUENCE: 132

Phe Xaa Ile Gly Arg Leu
1               5

<210> SEQ ID NO 133
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Val

<400> SEQUENCE: 133

Phe Val Ile Gly Arg Leu
1               5

<210> SEQ ID NO 134
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
```

-continued

```
<222> LOCATION: (2)..(2)
<223> OTHER INFORMATION: Xaa is L-beta-cyclohexyl-alanine

<400> SEQUENCE: 134

Phe Xaa Ile Gly Arg Leu
1               5

<210> SEQ ID NO 135
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-tert-butylglycine

<400> SEQUENCE: 135

Phe Xaa Ile Gly Arg Leu
1               5

<210> SEQ ID NO 136
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-1,4-diaminobutyric acid

<400> SEQUENCE: 136

Phe Xaa Ile Gly Arg Leu
1               5

<210> SEQ ID NO 137
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-(R,S)-3,4-cis-methanoproline

<400> SEQUENCE: 137

Phe Xaa Ile Gly Arg Leu
1               5

<210> SEQ ID NO 138
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-1,3-diaminopropionic acid

<400> SEQUENCE: 138

Phe Xaa Ile Gly Arg Leu
1               5

<210> SEQ ID NO 139
<211> LENGTH: 6
<212> TYPE: PRT
```

```
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-S-acetamidomethyl-penicillamine

<400> SEQUENCE: 139

Phe Xaa Ile Gly Arg Leu
1               5

<210> SEQ ID NO 140
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Homocysteine

<400> SEQUENCE: 140

Phe Xaa Ile Gly Arg Leu
1               5

<210> SEQ ID NO 141
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-beta-(2-pyridyl)-alanine

<400> SEQUENCE: 141

Phe Xaa Ile Gly Arg Leu
1               5

<210> SEQ ID NO 142
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 142

Phe Leu Ile Gly Arg Leu
1               5

<210> SEQ ID NO 143
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Leu
<220> FEATURE:
```

```
<221> NAME/KEY: misc_feature
<222> LOCATION: (6)..(6)
<223> OTHER INFORMATION: Leu is modified with a C terminal -NH2 moiety

<400> SEQUENCE: 143

Phe Leu Ile Gly Arg Leu
1               5

<210> SEQ ID NO 144
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (4)..(4)
<223> OTHER INFORMATION: May be D-Ile
<220> FEATURE:
<221> NAME/KEY: misc_feature
<222> LOCATION: (6)..(6)
<223> OTHER INFORMATION: Phe is modified with a C terminal -NH2 moiety

<400> SEQUENCE: 144

Leu Arg Gly Ile Leu Phe
1               5

<210> SEQ ID NO 145
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-alpha-aminobutyric acid(dimer)

<400> SEQUENCE: 145

Phe Xaa Ile Gly Arg Leu
1               5

<210> SEQ ID NO 146
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is dehydro-leucine or L-4,5-dehydro-
      leucine

<400> SEQUENCE: 146

Phe Xaa Ile Gly Arg Leu
1               5

<210> SEQ ID NO 147
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated
<220> FEATURE:
<221> NAME/KEY: misc_feature
<222> LOCATION: (2)..(2)
<223> OTHER INFORMATION: Xaa is Homoserine
```

```
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 147

Phe Xaa Ile Gly Arg
1               5

<210> SEQ ID NO 148
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Homoserine
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 148

Phe Xaa Ile Gly Arg
1               5

<210> SEQ ID NO 149
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated
<220> FEATURE:
<221> NAME/KEY: misc_feature
<222> LOCATION: (2)..(2)
<223> OTHER INFORMATION: Xaa is Homoserine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 149

Phe Xaa Ile Gly Arg Leu
1               5

<210> SEQ ID NO 150
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Homoserine
<220> FEATURE:
<221> NAME/KEY: misc_feature
<222> LOCATION: (3)..(3)
<223> OTHER INFORMATION: May be D-Ile

<400> SEQUENCE: 150

Phe Xaa Ile Gly Arg Leu
1               5
```

```
<210> SEQ ID NO 151
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-4-cyano-phenylalanine

<400> SEQUENCE: 151

Xaa Phe Ile Gly Arg Leu
1               5

<210> SEQ ID NO 152
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-3-methyl-phenylalanine

<400> SEQUENCE: 152

Xaa Phe Ile Gly Arg Leu
1               5

<210> SEQ ID NO 153
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-beta-cyclopropyl-alanine

<400> SEQUENCE: 153

Phe Xaa Ile Gly Arg Leu
1               5

<210> SEQ ID NO 154
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-propargylglycine
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 154

Phe Xaa Ile Gly Arg
1               5

<210> SEQ ID NO 155
<211> LENGTH: 5
<212> TYPE: PRT
<213> ORGANISM: Unknown
<220> FEATURE:
<223> OTHER INFORMATION: Peptide tight junction agonist
```

```
<220> FEATURE:
<221> NAME/KEY: misc_feature
<222> LOCATION: (2)..(2)
<223> OTHER INFORMATION: Xaa is L-beta-(2-furyl)-alanine
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 155

Phe Xaa Ile Gly Arg
1               5

<210> SEQ ID NO 156
<211> LENGTH: 5
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is 1,2,3,4-tetrahydroharmane-3-carboxylic
      acid
<220> FEATURE:
<221> NAME/KEY: misc_feature
<222> LOCATION: (5)..(5)
<223> OTHER INFORMATION: Arg is modified with a C terminal -NH2 moiety

<400> SEQUENCE: 156

Phe Xaa Ile Gly Arg
1               5

<210> SEQ ID NO 157
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-beta-styryl-alanine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 157

Phe Xaa Ile Gly Arg Leu
1               5

<210> SEQ ID NO 158
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is Homocitrulline
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 158

Phe Xaa Ile Gly Arg Leu
1               5

<210> SEQ ID NO 159
```

```
-continued

<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is 1,2,3,4-tetrahydroharmane-3-carboxylic
      acid
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 159

Phe Xaa Ile Gly Arg Leu
1               5

<210> SEQ ID NO 160
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: Xaa is L-beta-(2-furyl)-alanine
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 160

Phe Xaa Ile Gly Arg Leu
1               5

<210> SEQ ID NO 161
<211> LENGTH: 6
<212> TYPE: PRT
<213> ORGANISM: Unknown
<220> FEATURE:
<223> OTHER INFORMATION: Peptide tight junction agonist

<400> SEQUENCE: 161

Phe Cys Ile Gly Arg Leu
1               5

<210> SEQ ID NO 162
<211> LENGTH: 6
<212> TYPE: PRT
<213> ORGANISM: Unknown
<220> FEATURE:
<223> OTHER INFORMATION: Peptide tight junction agonist

<400> SEQUENCE: 162

Phe Cys Ala Gly Met Ser
1               5

<210> SEQ ID NO 163
<211> LENGTH: 6
<212> TYPE: PRT
<213> ORGANISM: Unknown
<220> FEATURE:
<223> OTHER INFORMATION: Peptide tight junction agonist

<400> SEQUENCE: 163

Phe Cys Val Gly Met Ser
1               5
```

```
<210> SEQ ID NO 164
<211> LENGTH: 6
<212> TYPE: PRT
<213> ORGANISM: Unknown
<220> FEATURE:
<223> OTHER INFORMATION: Peptide tight junction agonist

<400> SEQUENCE: 164

Pro Cys Ile Gly Arg Leu
1               5

<210> SEQ ID NO 165
<211> LENGTH: 6
<212> TYPE: PRT
<213> ORGANISM: Unknown
<220> FEATURE:
<223> OTHER INFORMATION: Peptide tight junction agonist

<400> SEQUENCE: 165

Gln Cys Ile Gly Arg Leu
1               5

<210> SEQ ID NO 166
<211> LENGTH: 6
<212> TYPE: PRT
<213> ORGANISM: Unknown
<220> FEATURE:
<223> OTHER INFORMATION: Peptide tight junction agonist

<400> SEQUENCE: 166

Gly Cys Ile Gly Arg Leu
1               5

<210> SEQ ID NO 167
<211> LENGTH: 6
<212> TYPE: PRT
<213> ORGANISM: Unknown
<220> FEATURE:
<223> OTHER INFORMATION: Peptide tight junction agonist

<400> SEQUENCE: 167

Thr Cys Ile Gly Arg Leu
1               5

<210> SEQ ID NO 168
<211> LENGTH: 6
<212> TYPE: PRT
<213> ORGANISM: Unknown
<220> FEATURE:
<223> OTHER INFORMATION: Peptide tight junction agonist

<400> SEQUENCE: 168

Ser Cys Ile Gly Arg Leu
1               5

<210> SEQ ID NO 169
<211> LENGTH: 6
<212> TYPE: PRT
<213> ORGANISM: Unknown
<220> FEATURE:
<223> OTHER INFORMATION: Peptide tight junction agonist

<400> SEQUENCE: 169

Asn Cys Ile Gly Arg Leu
1               5

<210> SEQ ID NO 170
```

```
<211> LENGTH: 6
<212> TYPE: PRT
<213> ORGANISM: Unknown
<220> FEATURE:
<223> OTHER INFORMATION: Peptide tight junction agonist

<400> SEQUENCE: 170

Arg Cys Ile Gly Arg Leu
1               5

<210> SEQ ID NO 171
<211> LENGTH: 6
<212> TYPE: PRT
<213> ORGANISM: Unknown
<220> FEATURE:
<223> OTHER INFORMATION: Peptide tight junction agonist

<400> SEQUENCE: 171

Val Cys Ile Gly Arg Leu
1               5

<210> SEQ ID NO 172
<211> LENGTH: 6
<212> TYPE: PRT
<213> ORGANISM: Unknown
<220> FEATURE:
<223> OTHER INFORMATION: Peptide tight junction agonist

<400> SEQUENCE: 172

Phe Cys Ile Gly Arg Gly
1               5

<210> SEQ ID NO 173
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Ala

<400> SEQUENCE: 173

Ala Cys Ile Gly Arg Gly
1               5

<210> SEQ ID NO 174
<211> LENGTH: 6
<212> TYPE: PRT
<213> ORGANISM: Unknown
<220> FEATURE:
<223> OTHER INFORMATION: Peptide tight junction agonist

<400> SEQUENCE: 174

Ala Cys Ile Gly Arg Gly
1               5

<210> SEQ ID NO 175
<211> LENGTH: 6
<212> TYPE: PRT
<213> ORGANISM: Unknown
<220> FEATURE:
<223> OTHER INFORMATION: Peptide tight junction agonist

<400> SEQUENCE: 175

Phe Cys Ile Gly Arg Gly
1               5
```

```
<210> SEQ ID NO 176
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe

<400> SEQUENCE: 176

Phe Cys Ile Gly Arg Gly
1               5

<210> SEQ ID NO 177
<211> LENGTH: 6
<212> TYPE: PRT
<213> ORGANISM: Unknown
<220> FEATURE:
<223> OTHER INFORMATION: Peptide tight junction agonist

<400> SEQUENCE: 177

Phe Cys Ile Gly Arg Ser
1               5

<210> SEQ ID NO 178
<211> LENGTH: 6
<212> TYPE: PRT
<213> ORGANISM: Unknown
<220> FEATURE:
<223> OTHER INFORMATION: Peptide tight junction agonist

<400> SEQUENCE: 178

Phe Cys Ile Gly Arg Gln
1               5

<210> SEQ ID NO 179
<211> LENGTH: 6
<212> TYPE: PRT
<213> ORGANISM: Unknown
<220> FEATURE:
<223> OTHER INFORMATION: Peptide tight junction agonist

<400> SEQUENCE: 179

Phe Cys Ile Gly Arg Lys
1               5

<210> SEQ ID NO 180
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: May be D-Ala

<400> SEQUENCE: 180

Phe Cys Ile Gly Arg Ala
1               5

<210> SEQ ID NO 181
<211> LENGTH: 6
<212> TYPE: PRT
<213> ORGANISM: Unknown
<220> FEATURE:
<223> OTHER INFORMATION: Peptide tight junction agonist
```

```
<400> SEQUENCE: 181

Phe Cys Ile Gly Arg Ile
1               5

<210> SEQ ID NO 182
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Gly is modified with a C terminal -NH2 moiety

<400> SEQUENCE: 182

Phe Cys Ile Gly Arg Gly
1               5

<210> SEQ ID NO 183
<211> LENGTH: 6
<212> TYPE: PRT
<213> ORGANISM: Unknown
<220> FEATURE:
<223> OTHER INFORMATION: Peptide tight junction agonist

<400> SEQUENCE: 183

Phe Cys Ile Gly Arg Asp
1               5

<210> SEQ ID NO 184
<211> LENGTH: 6
<212> TYPE: PRT
<213> ORGANISM: Unknown
<220> FEATURE:
<223> OTHER INFORMATION: Peptide tight junction agonist

<400> SEQUENCE: 184

Phe Cys Ile Gly Arg Glu
1               5

<210> SEQ ID NO 185
<211> LENGTH: 6
<212> TYPE: PRT
<213> ORGANISM: Unknown
<220> FEATURE:
<223> OTHER INFORMATION: Peptide tight junction agonist

<400> SEQUENCE: 185

Phe Cys Ile Gly Arg Phe
1               5

<210> SEQ ID NO 186
<211> LENGTH: 6
<212> TYPE: PRT
<213> ORGANISM: Unknown
<220> FEATURE:
<223> OTHER INFORMATION: Peptide tight junction agonist

<400> SEQUENCE: 186

Phe Cys Ile Gly Arg Asn
1               5

<210> SEQ ID NO 187
<211> LENGTH: 6
<212> TYPE: PRT
<213> ORGANISM: Unknown
```

```
<220> FEATURE:
<223> OTHER INFORMATION: Peptide tight junction agonist

<400> SEQUENCE: 187

Phe Cys Ile Gly Arg Pro
1               5

<210> SEQ ID NO 188
<211> LENGTH: 6
<212> TYPE: PRT
<213> ORGANISM: Unknown
<220> FEATURE:
<223> OTHER INFORMATION: Peptide tight junction agonist

<400> SEQUENCE: 188

Glu Cys Ile Gly Arg Leu
1               5

<210> SEQ ID NO 189
<211> LENGTH: 6
<212> TYPE: PRT
<213> ORGANISM: Unknown
<220> FEATURE:
<223> OTHER INFORMATION: Peptide tight junction agonist

<400> SEQUENCE: 189

Asp Cys Ile Gly Arg Leu
1               5

<210> SEQ ID NO 190
<211> LENGTH: 6
<212> TYPE: PRT
<213> ORGANISM: Unknown
<220> FEATURE:
<223> OTHER INFORMATION: Peptide tight junction agonist

<400> SEQUENCE: 190

Lys Cys Ile Gly Arg Leu
1               5

<210> SEQ ID NO 191
<211> LENGTH: 7
<212> TYPE: PRT
<213> ORGANISM: Unknown
<220> FEATURE:
<223> OTHER INFORMATION: Peptide tight junction agonist

<400> SEQUENCE: 191

Phe Cys Ile Gly Arg Leu Cys
1               5

<210> SEQ ID NO 192
<211> LENGTH: 6
<212> TYPE: PRT
<213> ORGANISM: Unknown
<220> FEATURE:
<223> OTHER INFORMATION: Peptide tight junction agonist

<400> SEQUENCE: 192

Pro Gly Pro Gly Arg Leu
1               5

<210> SEQ ID NO 193
<211> LENGTH: 6
<212> TYPE: PRT
<213> ORGANISM: Unknown
<220> FEATURE:
<223> OTHER INFORMATION: Peptide tight junction agonist
```

```
<400> SEQUENCE: 193

Phe Cys Ile Pro Gly Pro
1               5

<210> SEQ ID NO 194
<211> LENGTH: 6
<212> TYPE: PRT
<213> ORGANISM: Unknown
<220> FEATURE:
<223> OTHER INFORMATION: Peptide tight junction agonist

<400> SEQUENCE: 194

Phe Cys Leu Gly Arg Leu
1               5

<210> SEQ ID NO 195
<211> LENGTH: 6
<212> TYPE: PRT
<213> ORGANISM: Unknown
<220> FEATURE:
<223> OTHER INFORMATION: Peptide tight junction agonist

<400> SEQUENCE: 195

Gly Cys Ile Gly Arg Gly
1               5

<210> SEQ ID NO 196
<211> LENGTH: 6
<212> TYPE: PRT
<213> ORGANISM: Unknown
<220> FEATURE:
<223> OTHER INFORMATION: Peptide tight junction agonist

<400> SEQUENCE: 196

Tyr Cys Ile Gly Arg Leu
1               5

<210> SEQ ID NO 197
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Ala is acetylated

<400> SEQUENCE: 197

Ala Cys Ile Gly Arg Leu
1               5

<210> SEQ ID NO 198
<211> LENGTH: 6
<212> TYPE: PRT
<213> ORGANISM: Unknown
<220> FEATURE:
<223> OTHER INFORMATION: Peptide tight junction agonist

<400> SEQUENCE: 198

Trp Cys Ile Gly Arg Leu
1               5

<210> SEQ ID NO 199
<211> LENGTH: 6
<212> TYPE: PRT
<213> ORGANISM: Unknown
```

```
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Ala is acetylated

<400> SEQUENCE: 199

Ala Cys Ile Gly Arg Ser
1               5

<210> SEQ ID NO 200
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Ala is acetylated

<400> SEQUENCE: 200

Ala Cys Ile Gly Arg Ala
1               5

<210> SEQ ID NO 201
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated

<400> SEQUENCE: 201

Phe Cys Ile Gly Arg Phe
1               5

<210> SEQ ID NO 202
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 202

Ser Leu Ile Gly Arg Leu
1               5

<210> SEQ ID NO 203
<211> LENGTH: 4
<212> TYPE: PRT
<213> ORGANISM: Unknown
<220> FEATURE:
<223> OTHER INFORMATION: Peptide tight junction agonist

<400> SEQUENCE: 203

Phe Cys Ala Gly
1

<210> SEQ ID NO 204
<211> LENGTH: 4
<212> TYPE: PRT
```

```
<213> ORGANISM: Unknown
<220> FEATURE:
<223> OTHER INFORMATION: Peptide tight junction agonist

<400> SEQUENCE: 204

Phe Cys Gly Gly
1

<210> SEQ ID NO 205
<211> LENGTH: 7
<212> TYPE: PRT
<213> ORGANISM: Unknown
<220> FEATURE:
<223> OTHER INFORMATION: Peptide tight junction agonist

<400> SEQUENCE: 205

Gly Phe Cys Ile Gly Arg Leu
1               5

<210> SEQ ID NO 206
<211> LENGTH: 6
<212> TYPE: PRT
<213> ORGANISM: Unknown
<220> FEATURE:
<223> OTHER INFORMATION: Peptide tight junction agonist

<400> SEQUENCE: 206

Leu Arg Gly Gly Arg Leu
1               5

<210> SEQ ID NO 207
<211> LENGTH: 6
<212> TYPE: PRT
<213> ORGANISM: Unknown
<220> FEATURE:
<223> OTHER INFORMATION: Peptide tight junction agonist

<400> SEQUENCE: 207

Phe Cys Ala Gly Met Ser
1               5

<210> SEQ ID NO 208
<211> LENGTH: 6
<212> TYPE: PRT
<213> ORGANISM: Unknown
<220> FEATURE:
<223> OTHER INFORMATION: Peptide tight junction agonist

<400> SEQUENCE: 208

Phe Cys Val Gly Met Ser
1               5

<210> SEQ ID NO 209
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Phe is acetylated
<220> FEATURE:
<221> NAME/KEY: misc_feature
<222> LOCATION: (6)..(6)
<223> OTHER INFORMATION: Leu is modified with a C terminal -NH2 moiety

<400> SEQUENCE: 209

Phe Leu Ile Gly Arg Leu
```

```
1               5

<210> SEQ ID NO 210
<211> LENGTH: 5
<212> TYPE: PRT
<213> ORGANISM: Unknown
<220> FEATURE:
<223> OTHER INFORMATION: Peptide tight junction agonist

<400> SEQUENCE: 210

Tyr Ile Gly Ser Arg
1               5

<210> SEQ ID NO 211
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is Sarcosine

<400> SEQUENCE: 211

Xaa Cys Ile Gly Arg Leu
1               5

<210> SEQ ID NO 212
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-beta-cyclohexyl-alanine

<400> SEQUENCE: 212

Xaa Cys Ile Gly Arg Leu
1               5

<210> SEQ ID NO 213
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is alpha-aminoisobutyric acid

<400> SEQUENCE: 213

Xaa Cys Ile Gly Arg Leu
1               5

<210> SEQ ID NO 214
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-tert-butylglycine

<400> SEQUENCE: 214
```

```
Xaa Cys Ile Gly Arg Leu
1               5

<210> SEQ ID NO 215
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is Norvaline

<400> SEQUENCE: 215

Xaa Cys Ile Gly Arg Leu
1               5

<210> SEQ ID NO 216
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is Homoserine

<400> SEQUENCE: 216

Xaa Cys Ile Gly Arg Leu
1               5

<210> SEQ ID NO 217
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is Norvaline

<400> SEQUENCE: 217

Phe Cys Ile Gly Arg Xaa
1               5

<210> SEQ ID NO 218
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is beta-Alanine

<400> SEQUENCE: 218

Phe Cys Ile Gly Arg Xaa
1               5

<210> SEQ ID NO 219
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
```

```
<222> LOCATION: (6)..(6)
<223> OTHER INFORMATION: Xaa is L-tert-leucine

<400> SEQUENCE: 219

Phe Cys Ile Gly Arg Xaa
1               5

<210> SEQ ID NO 220
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is L-N-methyl-alanine

<400> SEQUENCE: 220

Phe Cys Ile Gly Arg Xaa
1               5

<210> SEQ ID NO 221
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is L-alpha-aminobutyric acid

<400> SEQUENCE: 221

Phe Cys Ile Gly Arg Xaa
1               5

<210> SEQ ID NO 222
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is alpha-aminoisobutyric acid

<400> SEQUENCE: 222

Phe Cys Ile Gly Arg Xaa
1               5

<210> SEQ ID NO 223
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is L-beta-cyclohexyl-alanine

<400> SEQUENCE: 223

Phe Cys Ile Gly Arg Xaa
1               5

<210> SEQ ID NO 224
<211> LENGTH: 6
<212> TYPE: PRT
```

```
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-alpha-aminobutyric acid

<400> SEQUENCE: 224

Xaa Cys Ile Gly Arg Leu
1               5

<210> SEQ ID NO 225
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is Orn

<400> SEQUENCE: 225

Xaa Cys Ile Gly Arg Leu
1               5

<210> SEQ ID NO 226
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (5)..(5)
<223> OTHER INFORMATION: Xaa is Citrulline

<400> SEQUENCE: 226

Phe Cys Ile Gly Xaa Leu
1               5

<210> SEQ ID NO 227
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-4-nitro-phenylalanine

<400> SEQUENCE: 227

Xaa Cys Ile Gly Arg Leu
1               5

<210> SEQ ID NO 228
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-4-chlorophenylalanine

<400> SEQUENCE: 228

Xaa Cys Ile Gly Arg Leu
1               5
```

```
<210> SEQ ID NO 229
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is L-4-chlorophenylalanine

<400> SEQUENCE: 229

Phe Cys Ile Gly Arg Xaa
1               5

<210> SEQ ID NO 230
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is L-4-nitro-phenylalanine

<400> SEQUENCE: 230

Phe Cys Ile Gly Arg Xaa
1               5

<210> SEQ ID NO 231
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-1,2,3,4-tetrahydroisoquinoline-3-
      carboxylic acid

<400> SEQUENCE: 231

Xaa Cys Ile Gly Arg Leu
1               5

<210> SEQ ID NO 232
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (3)..(3)
<223> OTHER INFORMATION: Xaa is N-methylated Isoleucine

<400> SEQUENCE: 232

Phe Cys Xaa Gly Arg Leu
1               5

<210> SEQ ID NO 233
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
```

```
<223> OTHER INFORMATION: Xaa is L-beta-(2-thienyl)-alanine

<400> SEQUENCE: 233

Phe Cys Ile Gly Arg Xaa
1               5

<210> SEQ ID NO 234
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: Xaa is L-beta-(2-thienyl)-alanine

<400> SEQUENCE: 234

Xaa Cys Ile Gly Arg Leu
1               5

<210> SEQ ID NO 235
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is L-1,2,3,4-tetrahydroisoquinoline-3-
      carboxylic acid

<400> SEQUENCE: 235

Phe Cys Ile Gly Arg Xaa
1               5

<210> SEQ ID NO 236
<211> LENGTH: 6
<212> TYPE: PRT
<213> ORGANISM: Unknown
<220> FEATURE:
<223> OTHER INFORMATION: Peptide tight junction agonist

<400> SEQUENCE: 236

Phe Cys Ile Gly Arg Leu
1               5

<210> SEQ ID NO 237
<211> LENGTH: 6
<212> TYPE: PRT
<213> ORGANISM: Unknown
<220> FEATURE:
<223> OTHER INFORMATION: Peptide tight junction agonist

<400> SEQUENCE: 237

Ala Cys Ile Gly Arg Leu
1               5

<210> SEQ ID NO 238
<211> LENGTH: 6
<212> TYPE: PRT
<213> ORGANISM: Unknown
<220> FEATURE:
<223> OTHER INFORMATION: Peptide tight junction agonist

<400> SEQUENCE: 238

Phe Ala Ile Gly Arg Leu
1               5
```

```
<210> SEQ ID NO 239
<211> LENGTH: 6
<212> TYPE: PRT
<213> ORGANISM: Unknown
<220> FEATURE:
<223> OTHER INFORMATION: Peptide tight junction agonist

<400> SEQUENCE: 239

Phe Cys Ala Gly Arg Leu
1               5

<210> SEQ ID NO 240
<211> LENGTH: 6
<212> TYPE: PRT
<213> ORGANISM: Unknown
<220> FEATURE:
<223> OTHER INFORMATION: Peptide tight junction agonist

<400> SEQUENCE: 240

Phe Cys Ile Ala Arg Leu
1               5

<210> SEQ ID NO 241
<211> LENGTH: 6
<212> TYPE: PRT
<213> ORGANISM: Unknown
<220> FEATURE:
<223> OTHER INFORMATION: Peptide tight junction agonist

<400> SEQUENCE: 241

Phe Cys Ile Gly Ala Leu
1               5

<210> SEQ ID NO 242
<211> LENGTH: 6
<212> TYPE: PRT
<213> ORGANISM: Unknown
<220> FEATURE:
<223> OTHER INFORMATION: Peptide tight junction agonist

<400> SEQUENCE: 242

Phe Cys Ile Gly Arg Ala
1               5

<210> SEQ ID NO 243
<211> LENGTH: 5
<212> TYPE: PRT
<213> ORGANISM: Unknown
<220> FEATURE:
<223> OTHER INFORMATION: Peptide tight junction agonist

<400> SEQUENCE: 243

Cys Ile Gly Arg Leu
1               5

<210> SEQ ID NO 244
<211> LENGTH: 4
<212> TYPE: PRT
<213> ORGANISM: Unknown
<220> FEATURE:
<223> OTHER INFORMATION: Peptide tight junction agonist

<400> SEQUENCE: 244

Ile Gly Arg Leu
1
```

```
<210> SEQ ID NO 245
<211> LENGTH: 5
<212> TYPE: PRT
<213> ORGANISM: Unknown
<220> FEATURE:
<223> OTHER INFORMATION: Peptide tight junction agonist

<400> SEQUENCE: 245

Phe Cys Ile Gly Arg
1               5

<210> SEQ ID NO 246
<211> LENGTH: 4
<212> TYPE: PRT
<213> ORGANISM: Unknown
<220> FEATURE:
<223> OTHER INFORMATION: Peptide tight junction agonist

<400> SEQUENCE: 246

Phe Cys Ile Gly
1

<210> SEQ ID NO 247
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe

<400> SEQUENCE: 247

Phe Cys Ile Gly Arg Leu
1               5

<210> SEQ ID NO 248
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Cys

<400> SEQUENCE: 248

Phe Cys Ile Gly Arg Leu
1               5

<210> SEQ ID NO 249
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (3)..(3)
<223> OTHER INFORMATION: May be D-Ile

<400> SEQUENCE: 249

Phe Cys Ile Gly Arg Leu
1               5

<210> SEQ ID NO 250
<211> LENGTH: 6
<212> TYPE: PRT
```

```
<213> ORGANISM: Unknown
<220> FEATURE:
<223> OTHER INFORMATION: Peptide tight junction agonist
<220> FEATURE:
<221> NAME/KEY: misc_feature
<222> LOCATION: (5)..(5)
<223> OTHER INFORMATION: May be D-Arg

<400> SEQUENCE: 250

Phe Cys Ile Gly Arg Leu
1               5

<210> SEQ ID NO 251
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: Xaa is D-Leu

<400> SEQUENCE: 251

Phe Cys Ile Gly Arg Leu
1               5

<210> SEQ ID NO 252
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature
<222> LOCATION: (4)..(4)
<223> OTHER INFORMATION: May be D-Ile
<220> FEATURE:
<221> NAME/KEY: misc_feature
<222> LOCATION: (5)..(5)
<223> OTHER INFORMATION: May be D-Cys
<220> FEATURE:
<221> NAME/KEY: misc_feature
<222> LOCATION: (6)..(6)
<223> OTHER INFORMATION: May be D-Phe

<400> SEQUENCE: 252

Leu Arg Gly Ile Cys Phe
1               5

<210> SEQ ID NO 253
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature
```

```
<222> LOCATION: (4)..(4)
<223> OTHER INFORMATION: May be D-Ile
<220> FEATURE:
<221> NAME/KEY: misc_feature
<222> LOCATION: (5)..(5)
<223> OTHER INFORMATION: May be D-Cys

<400> SEQUENCE: 253

Leu Arg Gly Ile Cys Phe
1               5

<210> SEQ ID NO 254
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature
<222> LOCATION: (4)..(4)
<223> OTHER INFORMATION: May be D-Ile
<220> FEATURE:
<221> NAME/KEY: misc_feature
<222> LOCATION: (6)..(6)
<223> OTHER INFORMATION: May be D-Phe

<400> SEQUENCE: 254

Leu Arg Gly Ile Cys Phe
1               5

<210> SEQ ID NO 255
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature
<222> LOCATION: (5)..(5)
<223> OTHER INFORMATION: May be D-Cys
<220> FEATURE:
<221> NAME/KEY: misc_feature
<222> LOCATION: (6)..(6)
<223> OTHER INFORMATION: May be D-Phe

<400> SEQUENCE: 255

Leu Arg Gly Ile Cys Phe
1               5

<210> SEQ ID NO 256
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
```

-continued

```
<223> OTHER INFORMATION: May be D-Leu
<220> FEATURE:
<221> NAME/KEY: misc_feature
<222> LOCATION: (4)..(4)
<223> OTHER INFORMATION: May be D-Ile
<220> FEATURE:
<221> NAME/KEY: misc_feature
<222> LOCATION: (5)..(5)
<223> OTHER INFORMATION: May be D-Cys
<220> FEATURE:
<221> NAME/KEY: misc_feature
<222> LOCATION: (6)..(6)
<223> OTHER INFORMATION: May be D-Phe

<400> SEQUENCE: 256

Leu Arg Gly Ile Cys Phe
1               5

<210> SEQ ID NO 257
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature
<222> LOCATION: (4)..(4)
<223> OTHER INFORMATION: May be D-Ile
<220> FEATURE:
<221> NAME/KEY: misc_feature
<222> LOCATION: (5)..(5)
<223> OTHER INFORMATION: May be D-Cys
<220> FEATURE:
<221> NAME/KEY: misc_feature
<222> LOCATION: (6)..(6)
<223> OTHER INFORMATION: May be D-Phe

<400> SEQUENCE: 257

Leu Arg Gly Ile Cys Phe
1               5

<210> SEQ ID NO 258
<211> LENGTH: 6
<212> TYPE: PRT
<213> ORGANISM: Unknown
<220> FEATURE:
<223> OTHER INFORMATION: Peptide tight junction agonist

<400> SEQUENCE: 258

Leu Arg Gly Ile Cys Phe
1               5

<210> SEQ ID NO 259
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu

<400> SEQUENCE: 259

Leu Arg Gly Ile Cys Phe
1               5

<210> SEQ ID NO 260
```

```
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Arg

<400> SEQUENCE: 260

Leu Arg Gly Ile Cys Phe
1               5

<210> SEQ ID NO 261
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (4)..(4)
<223> OTHER INFORMATION: May be D-Ile

<400> SEQUENCE: 261

Leu Arg Gly Ile Cys Phe
1               5

<210> SEQ ID NO 262
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (5)..(5)
<223> OTHER INFORMATION: May be D-Cys

<400> SEQUENCE: 262

Leu Arg Gly Ile Cys Phe
1               5

<210> SEQ ID NO 263
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (6)..(6)
<223> OTHER INFORMATION: May be D-Phe

<400> SEQUENCE: 263

Leu Arg Gly Ile Cys Phe
1               5

<210> SEQ ID NO 264
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe
<220> FEATURE:
<221> NAME/KEY: misc_feature
<222> LOCATION: (2)..(2)
```

```
<223> OTHER INFORMATION: May be D-Cys
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (5)..(5)
<223> OTHER INFORMATION: May be D-Arg
<220> FEATURE:
<221> NAME/KEY: misc_feature
<222> LOCATION: (6)..(6)
<223> OTHER INFORMATION: May be D-Leu

<400> SEQUENCE: 264

Phe Cys Ile Gly Arg Leu
1               5

<210> SEQ ID NO 265
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe
<220> FEATURE:
<221> NAME/KEY: misc_feature
<222> LOCATION: (2)..(2)
<223> OTHER INFORMATION: May be D-Cys
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (5)..(5)
<223> OTHER INFORMATION: May be D-Arg

<400> SEQUENCE: 265

Phe Cys Ile Gly Arg Leu
1               5

<210> SEQ ID NO 266
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe
<220> FEATURE:
<221> NAME/KEY: misc_feature
<222> LOCATION: (2)..(2)
<223> OTHER INFORMATION: May be D-Cys
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (6)..(6)
<223> OTHER INFORMATION: May be D-Leu

<400> SEQUENCE: 266

Phe Cys Ile Gly Arg Leu
1               5

<210> SEQ ID NO 267
<211> LENGTH: 6
```

```
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe
<220> FEATURE:
<221> NAME/KEY: misc_feature
<222> LOCATION: (2)..(2)
<223> OTHER INFORMATION: May be D-Cys
<220> FEATURE:
<221> NAME/KEY: misc_feature
<222> LOCATION: (5)..(5)
<223> OTHER INFORMATION: May be D-Arg
<220> FEATURE:
<221> NAME/KEY: misc_feature
<222> LOCATION: (6)..(6)
<223> OTHER INFORMATION: May be D-Leu

<400> SEQUENCE: 267

Phe Cys Ile Gly Arg Leu
1               5

<210> SEQ ID NO 268
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Phe
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (5)..(5)
<223> OTHER INFORMATION: May be D-Arg
<220> FEATURE:
<221> NAME/KEY: misc_feature
<222> LOCATION: (6)..(6)
<223> OTHER INFORMATION: May be D-Leu

<400> SEQUENCE: 268

Phe Cys Ile Gly Arg Leu
1               5

<210> SEQ ID NO 269
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Cys
<220> FEATURE:
<221> NAME/KEY: misc_feature
<222> LOCATION: (3)..(3)
<223> OTHER INFORMATION: May be D-Ile
<220> FEATURE:
<221> NAME/KEY: misc_feature
<222> LOCATION: (5)..(5)
<223> OTHER INFORMATION: May be D-Arg
<220> FEATURE:
<221> NAME/KEY: misc_feature
<222> LOCATION: (6)..(6)
<223> OTHER INFORMATION: May be D-Leu

<400> SEQUENCE: 269
```

Phe Cys Ile Gly Arg Leu
1               5

<210> SEQ ID NO 270
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (2)..(2)
<223> OTHER INFORMATION: May be D-Cys
<220> FEATURE:
<221> NAME/KEY: misc_feature
<222> LOCATION: (5)..(5)
<223> OTHER INFORMATION: May be D-Arg

<400> SEQUENCE: 270

Phe Cys Ile Gly Arg Leu
1               5

<210> SEQ ID NO 271
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu

<400> SEQUENCE: 271

Leu Arg Gly Ile Cys Phe
1               5

<210> SEQ ID NO 272
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg

<400> SEQUENCE: 272

Leu Arg Gly Ile Cys Phe
1               5

<210> SEQ ID NO 273
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature

```
<222> LOCATION: (6)..(6)
<223> OTHER INFORMATION: May be D-Phe

<400> SEQUENCE: 273

Leu Arg Gly Ile Cys Phe
1               5

<210> SEQ ID NO 274
<211> LENGTH: 6
<212> TYPE: PRT
<213> ORGANISM: Unknown
<220> FEATURE:
<223> OTHER INFORMATION: Peptide tight junction agonist
<220> FEATURE:
<221> NAME/KEY: misc_feature
<222> LOCATION: (1)..(1)
<223> OTHER INFORMATION: May be D-Leu
<220> FEATURE:
<221> NAME/KEY: misc_feature
<222> LOCATION: (2)..(2)
<223> OTHER INFORMATION: May be D-Arg
<220> FEATURE:
<221> NAME/KEY: misc_feature
<222> LOCATION: (5)..(5)
<223> OTHER INFORMATION: May be D-Cys

<400> SEQUENCE: 274

Leu Arg Gly Ile Cys Phe
1               5
```

SYNTHETIC PEPTIDES THAT ENHANCE TIGHT JUNCTION PERMEABILITY

PRIORITY

This application is a National Stage of PCT/US08/71321, filed Jul. 28, 2008, which claims the benefit of U.S. Provisional Application No. 60/977,242 filed Oct. 3, 2007, U.S. Provisional Application No. 60/952,144 filed Jul. 26, 2007, U.S. Provisional Application No. 60/953,398 filed Aug. 1, 2007, U.S. Provisional Application No. 60/953,403 filed Aug. 1, 2007, and U.S. Provisional Application No. 60/953,405 filed Aug. 1, 2007, each of which is hereby incorporated by reference in its entirety.

FIELD OF THE INVENTION

The present invention provides novel peptides that enhance tight junction permeability and their use as therapeutic agents, and their use in materials and methods to facilitate the delivery of therapeutic agents. In some embodiments, novel peptides that enhance tight junction permeability (i.e., peptide tight junction agonists) are used in compositions to facilitate the uptake of therapeutic agents across biological barriers comprising tight junctions. In some embodiments, such peptide tight junction agonists are used in compositions to modulate an immune response in a subject. In some embodiments, such peptide tight junction agonists are used in compositions to raise an immune response against an antigen.

BACKGROUND

The tight junctions (tj) or zonula occludens (ZO) are one of the hallmarks of absorptive and secretory epithelia (Madara, J. Clin. Invest., 83:1089-1094 (1989); and Madara, Textbook of Secretory Diarrhea Eds. Lebenthal et al, Chapter 11, pages 125-138 (1990)). Tight junctions act as a barrier between apical and basolateral compartments, selectively regulating the passive diffusion of ions and water-soluble solutes through the paracellular (between cells) pathway (Gumbiner, Am. J. Physiol., 253 (Cell Physiol. 22):C749-C758 (1987)). This barrier maintains any gradient generated by the activity of pathways associated with the transcellular route (Diamond, Physiologist, 20:10-18 (1977)).

Variations in transepithelial conductance can usually be attributed to changes in the permeability of the paracellular pathway, since the resistances of enterocyte plasma membranes are relatively high (Madara, supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, J. Cell Biol., 101:2124-2133 (1985)).

Zonula occludens toxin (ZOT), which is produced by *Vibrio cholerae*, has been characterized by Fasano et al., (*Proc. Natl. Acad. Sci., USA*, 8:5242-5246 (1991)) and the sequence has been determined (GenBank accession no. A43864). ZOT is a tight junction agonist and increases the intestinal permeability of rabbit ileal mucosa by modulating the structure of intercellular tight junctions. U.S. Pat. Nos. 5,827,534, 5,665,389, 5,908,825 disclose the use of ZOT to facilitate the uptake of therapeutic agents. U.S. patent publication nos. US-2006-0276403-A1 and US 2006-0165722A1, and application Ser. No. 11/673,192 disclose peptide tight junction agonists that can be used to facilitate the uptake of therapeutic agents.

Drug Delivery

The low bioavailability (BA) of efficacious pharmacotherapeutic drugs continues to be a major obstacle in drug development and in many instances may be the deciding factor on whether or not a potent agent is developed. Many therapeutic agents experience low BA after oral administration due to poor absorption or susceptibility to first pass metabolism. A means of enhancing the gastrointestinal absorption of such drugs would significantly extend their therapeutic usefulness while decreasing the dose required to produce efficacy.

Absorption enhancers, including surfactants, fatty acids, and chitosan derivatives, have been used to modify bioavailability by either disruption of the cell membrane or modulation of the tight junctions (TJ). In general, the optimal absorption enhancer should possess the following qualities: its effect should be reversible, it should provide a rapid permeation enhancing effect on the intestinal cellular membrane, it should be non-cytotoxic at the effective concentration level without deleterious and/or irreversible effects on the cellular membrane or cytoskeleton of the TJ. Zonula Occludens Toxin (Zot), a 44.8 kDa protein (399 amino acids; AA) located in the cell envelope of the bacterial strain *Vibrio cholerae*, is capable of reversibly opening the TJ between cells and increasing the paracellular transport of many drugs in a non-toxic manner. Intensive investigation of the biological activity of Zot as an absorption enhancer was triggered by reports of effective oral administration of insulin with Zot in diabetic rats. Recently, a smaller 12 kDa fragment (AA 265-399) of Zot, referred to as delta G (ΔG), was introduced as the biologically active fragment of Zot. Amino acid comparison between Zot active fragment and Zonulin, combined with site-directed mutagenesis experiments, confirmed the presence of an octapeptide receptor-binding domain toward the amino terminus of the processed Zot.

Applicants disclose novel peptides that enhance tight junction permeability, and methods of increasing bioavailability of pharmacotherapeutic drugs. The novel peptides facilitate transport of pharmacotherapeutic drugs across biological barriers whose permeability is regulated by tight junctions and thereby allows for increased bioavailability of such drugs. The novel peptides of the present invention are advantageous in that they are non-toxic, their effects are reversible, they are devoid of endotoxin contamination, readily synthesized and inexpensive to produce and purify.

Vaccines

Vaccines have proven to be successful, highly acceptable methods for the prevention of infectious diseases. They are cost effective, and do not induce antibiotic resistance to the target pathogen or affect normal flora present in the host. In many cases, such as when inducing anti-viral immunity, vaccines can prevent a disease for which there are no viable curative or ameliorative treatments available.

As is well known in the art, vaccines function by triggering the immune system to mount a response to an immunogenic agent, or antigen (antigenic agent), typically an infectious organism or a portion thereof that is introduced into the body in a non-infectious or non-pathogenic form. Once the immune system has been "primed" or sensitized to the organism, later exposure of the immune system to this organism as an infectious pathogen results in a rapid and robust immune response that destroys the pathogen before it can multiply and infect enough cells in the host organism to cause disease symptoms. The agent or antigen used to induce the immune system can be the entire organism in a less infectious state, known as an attenuated organism, or in some cases, components of the organism such as carbohydrates, proteins or peptides representing various structural components of the organism.

In many cases, it is necessary to enhance the immune response to the antigens present in a vaccine in order to stimulate the immune system to a sufficient extent to make a vaccine effective, i.e., to confer immunity. Many protein and most peptide and carbohydrate antigens, administered alone, do not elicit a sufficient antibody response to confer immunity. Such antigens need to be presented to the immune system in such a way that they will be recognized as foreign and will elicit an immune response. To this end, adjuvants have been devised which stimulate the immune response.

The best known adjuvant, Freund's complete adjuvant, consists of a mixture of mycobacteria in an oil/water emulsion. Freund's adjuvant works in two ways: first, by enhancing cell and humoral-mediated immunity, and second, by blocking rapid dispersal of the antigen challenge (the "depot effect"). However, due to frequent toxic physiological and immunological reactions to this material, Freund's adjuvant cannot be used in humans. Another molecule that has been shown to have immunostimulatory or adjuvant activity is endotoxin, also known as lipopolysaccharide (LPS). LPS stimulates the immune system by triggering an "innate" immune response—a response that has evolved to enable an organism to recognize endotoxin (and the invading bacteria of which it is a component) without the need for the organism to have been previously exposed. While LPS is too toxic to be a viable adjuvant, molecules that are structurally related to endotoxin, such as monophosphoryl lipid A ("MPL") are being tested as adjuvants in clinical trials. Currently, however, the only FDA-approved adjuvant for use in humans is aluminum salts (Alum) which are used to "depot" antigens by precipitation of the antigens. Alum also stimulates the immune response to antigens.

Thus, there is a recognized need in the art for compounds which can be co-administered with antigens in order to stimulate the immune system to generate a more robust antibody response to the antigen than would be seen if the antigen were injected alone or with Alum. Further, because development of mucosal vaccines requires the use of specific adjuvants, adjuvants that work for systemic immunization such as Alum are generally not effective for mucosal immunization. Despite intensive research on adjuvants for mucosal vaccines in the last decade, no adjuvants have been registered for human use so far. The main issues in adjuvant research are efficacy and toxicity, and candidate mucosal adjuvants do not completely satisfy the criteria of high efficacy and absence of toxicity. Furthermore, most of the proposed mucosal adjuvants are complex molecules whose mechanism of action is poorly understood. Applicants provide herein non-toxic alternative peptide tight junction agonist adjuvants for inducing immune responses to an antigen.

Zonula Occludens Toxin (ZOT) from *Vibrio cholerae* was identified as an adjuvant for mucosal vaccination (Infect. Immun. 1999, 67:1287; Infect. Immun. 2003, 71:1897). Intranasal administration of ZOT with a soluble antigen in mice stimulated systemic humoral and cell-mediated responses as well as mucosal responses specific for the antigen Ovalbumin (Infect. Immun. 2003, 71:1897). ZOT is a protein of 44.8 kDa that binds a receptor on epithelial cells and modulates tight junctions, inducing the increase of mucosal barrier permeability. The effect of ZOT on tight junctions is reversible and does not cause tissue damage (J. Clin. Invest. 1995, 96:710). The receptor for ZOT on epithelial cells has been partially characterized and recently a mammalian protein with homology to ZOT has been identified and named Zonulin. Interestingly, this protein has been shown to be an endogenous regulator of tight junctions that is released by epithelial cells and binds to the same receptor used by ZOT (Ann. NY. Acad Sci. 2000, 915:214). The mechanism of ZOT as an adjuvant may involve binding to its receptor on the nasal mucosa, modulation of tight junctions and antigen passage in the submucosa, with subsequent exposure to cells of the immune system.

The development of mucosal vaccines for the prevention of infectious diseases is highly desirable. Mucosal vaccination has several advantages over parenteral vaccination. Mucosal immunization induces an immune response at the site of infection (locally). Furthermore, because of the intrinsic properties of the mucosal immune system, the immunization at one mucosal site can induce specific responses at distant sites (regionally). Such flexibility is important to address cultural and religious barriers to vaccination because protective immunity (for instance against sexually-transmitted diseases) may then be induced in segregated mucosal sites in a practical way. In addition to local responses against mucosally-acquired pathogens, mucosal vaccines induce systemic immunity, including humoral and cell-mediated responses. Thus, mucosal vaccination could be exploited for combating infections acquired through other routes (i.e., blood or skin). Finally, the administration of mucosal vaccines does not require the use of needles, which could increase vaccine compliance and negate concerns with blood transmissible infections. For all the above reasons mucosal vaccines may be used also to combat cancer, either with preventive or therapeutic vaccination. These vaccines may be both against cancers caused by infectious agents (such as *Helicobacter pylori, Papilloma Virus*, Herpes Virus) and cancers of different etiology (such as melanoma, colon cancer and others).

Interestingly, most human pathogens are acquired through the mucosal route, however, few mucosal vaccines are presently used. Of those currently used, the vaccine is based on a living attenuated microorganism. Further, purified antigens are not able to stimulate/induce an immune response per se when delivered at mucosal surfaces. Therefore, such vaccines require the use of specific adjuvants. Unfortunately, development of mucosal vaccines has been so far hampered by the lack of safe and effective adjuvants as described above. An effective mucosal adjuvant allows antigen (Ag) passage through a mucosal barrier and facilitates the induction of an Ag-specific immune response.

Applicants disclose novel peptides that enhance tight junction permeability, and methods of mucosal delivery of an antigen together with such peptides to induce systemic and/or mucosal responses specific for the antigen. The novel peptides facilitate delivery of the antigen through the mucosa and induce systemic and mucosal responses to the antigen. The novel peptides of the present invention are advantageous in that they are non-toxic, their effects are reversible, they are devoid of endotoxin contamination, readily synthesized and inexpensive to produce and purify.

There remains a need in the art for materials and methods to modulate immune responses and to facilitate the delivery of therapeutic agents. This need and others are met by the present invention.

SUMMARY OF THE INVENTION

The present invention provides novel peptide tight junction agonists (inducers). Generally, the peptide tight junction agonists comprise the amino acid sequence of SEQ ID NO:1, with at least one amino acid deletion, insertion, or substitution, or at least one chemical modification, with respect to SEQ ID NO: 1. For example, the peptide tight junction agonist may have from one to five amino acid substitutions with respect to SEQ ID NO: 1, while maintaining the activity as an agonist (inducer) of tight junction permeability. In certain embodiments, the tight junction agonist has an AllylGly at the position corresponding to position 2 of SEQ ID NO: 1.

Such peptide tight junction agonists of the invention may vary in length. In some embodiments, peptide tight junction agonists according to the invention may be from about three to about ten amino acids in length. In some embodiments, peptide tight junction agonists of the invention may comprise, consist essentially of, or consist of a peptide that comprises, consists essentially of, or consists of an amino acid sequence selected from the group consisting of SEQ ID NOs: 2-90. In some embodiments, peptide tight junction agonists of the invention may comprise, consist essentially of, or consist of a peptide that comprises, consists essentially of, or consists of the amino acid sequence of SEQ ID NO:2. In other embodiments, peptide tight junction agonists of the invention may comprise, consist essentially of, or consist of a peptide that comprises, consists essentially of, or consists of an amino acid sequence selected from the group consisting of SEQ ID NOs:5-21. In other embodiments, peptide tight junction agonists of the invention may comprise, consist essentially of, or consist of a peptide that comprises, consists essentially of, or consists of an amino acid sequence selected from the group consisting of SEQ ID NOs:22-38. In other embodiments, peptide tight junction agonists of the invention may comprise, consist essentially of, or consist of a peptide that comprises, consists essentially of, or consists of an amino acid sequence selected from the group consisting of SEQ ID NOs:39-54. In other embodiments, peptide tight junction agonists of the invention may comprise, consist essentially of, or consist of a peptide that comprises, consists essentially of, or consists of an amino acid sequence selected from the group consisting of SEQ ID NOs:55-72. In other embodiments, peptide tight junction agonists of the invention may comprise, consist essentially of, or consist of a peptide that comprises, consists essentially of, or consists of an amino acid sequence selected from the group consisting of SEQ ID NOs:73-90. In some embodiments, peptide tight junction agonists of the invention may comprise, consist essentially of, or consist of a peptide that comprises, consists essentially of, or consists of an amino acid sequence selected from the group consisting of SEQ ID NOs:15, 23, 25, 26, 27, 29, 30 and 42. Additional tight junction agonists of the invention are as shown in the sequence listing filed concurrently herewith.

The present invention also provides compositions, e.g., pharmaceutical compositions, comprising one or more peptide tight junction agonists of the invention. Suitable peptide tight junction agonists for use in the compositions of the invention include, but are not limited to, peptide tight junction agonists that comprise, consist essentially of, or consist of a peptide that comprises, consists essentially of, or consists of an amino acid sequence selected from the group consisting of SEQ ID NOs:2-90. In some embodiments, peptide tight junction agonists for use in the compositions of the invention may comprise, consist essentially of, or consist of a peptide that comprises, consists essentially of, or consists of the amino acid sequence of SEQ ID NO:2. In other embodiments, peptide tight junction agonists for use in the compositions of the invention may comprise, consist essentially of, or consist of a peptide that comprises, consists essentially of, or consists of an amino acid sequence selected from the group consisting of SEQ ID NOs:5-21. In other embodiments, peptide tight junction agonists for use in the compositions of the invention may comprise, consist essentially of, or consist of a peptide that comprises, consists essentially of, or consists of an amino acid sequence selected from the group consisting of SEQ ID NOs:22-38. In other embodiments, peptide tight junction agonists for use in the compositions of the invention may comprise, consist essentially of, or consist of a peptide that comprises, consists essentially of, or consists an amino acid sequence selected from the group consisting of SEQ ID NOs: 39-54. In other embodiments, peptide tight junction agonists for use in the compositions of the invention may comprise, consist essentially of or consist of a peptide that comprises, consists essentially of, or consists of an amino acid sequence selected from the group consisting of SEQ ID NOs:55-72. In other embodiments, peptide tight junction agonists for use in the compositions of the invention may comprise, consist essentially of, or consist of a peptide that comprises, consists essentially of, or consists of an amino acid sequence selected from the group consisting of SEQ ID NOs:73-90. In some embodiments, peptide tight junction agonists for use in the compositions of the invention include, but are not limited to, peptide tight junction agonists that comprise, consist essentially of, or consist of a peptide that comprises, consists essentially of, or consists of an amino acid sequence selected from the group consisting of SEQ ID NOs:15, 23, 25, 26, 27, 29, 30 and 42. Compositions of the invention may further comprise one or more additional active agents. Typically additional active agents may be therapeutic agents, imaging agents, and/or immunogenic agents. Examples of suitable additional therapeutic agents include, but are not limited to, glucose metabolism agents (e.g., insulin), antibiotics, antineoplastics, antihypertensives, antiepileptics, central nervous system agents, and immune system suppressants. Examples of suitable additional immunogenic agents include, but are not limited to, antigens. Suitable additional imaging agents include, but are not limited to, agents comprising one or more radioactive atoms. A pharmaceutical composition of the invention may comprise one or more pharmaceutically acceptable excipients.

Compositions of the invention, for example, pharmaceutical compositions, may be formulated for any type of delivery. For example, compositions of the invention may be formulated for intestinal delivery, e.g., may be delayed release compositions. Compositions of the invention may also be formulated for pulmonary delivery, oral delivery and/or transcutaneous delivery.

In one embodiment, the present invention provides a method of treating a disease in a subject in need thereof. Methods of the invention may comprise administering to the subject a pharmaceutical composition comprising one or more peptide tight junction agonists and one or more additional therapeutic agents. In one embodiment, the present invention provides a method of treating diabetes in a subject in need thereof. In another embodiment, the present invention provides a method of treating an excessive or undesirable immune response in a subject in need thereof. In another embodiment, the present invention provides a method of treating inflammation in a subject in need thereof. In specific embodiments, the present invention provides methods of treating inflammatory bowel disease in a subject in need thereof. Inflammatory bowel disease that can be treated using methods of the present invention may be Crohn's disease or ulcerative colitis. In another embodiment, the present invention provides methods of treating cancer in a subject in need thereof.

In certain embodiments, pharmaceutical compositions of the present invention may comprise one or more insulins and/or derivatives thereof. In other embodiments, pharmaceutical compositions of the present invention may comprise one or more anti-inflammatory agents. In other embodiments, pharmaceutical compositions of the present invention may comprise one or more immune-suppressive drugs, for example, cyclosporin A. In another embodiment, pharmaceutical compositions of the present invention may comprise one or more anticancer agents.

BRIEF DESCRIPTION OF THE DRAWINGS

Figure 11:
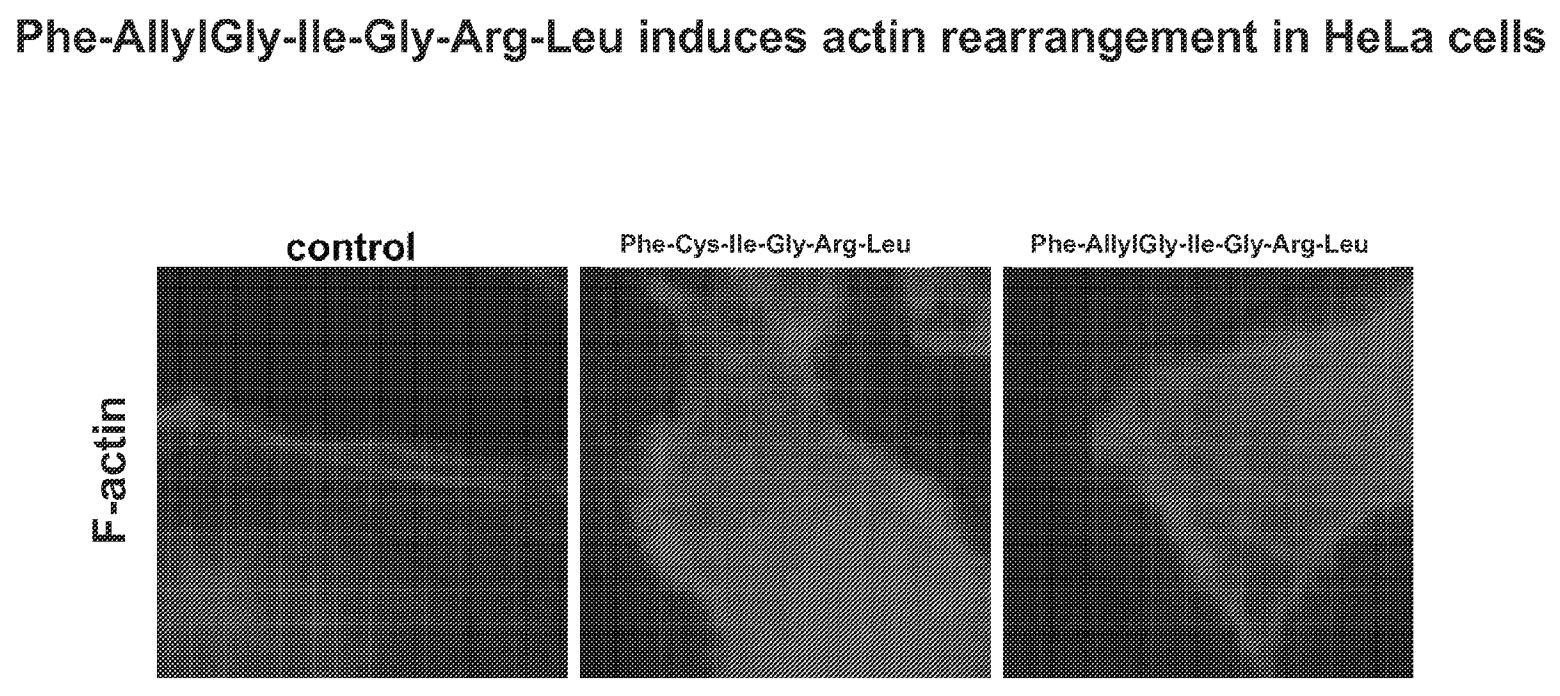

FIG. 11 is a magnified version of the 60 minute panels of FIG. 10, showing actin cytoskeletal rearrangement to the borderline of cells with the tight junction agonists FCIGRL (SEQ ID NO:1) and F-(Allyl)GIGRL (SEQ ID NO:2).

DETAILED DESCRIPTION OF THE INVENTION

Tight Junction Agonists

Figure 1:
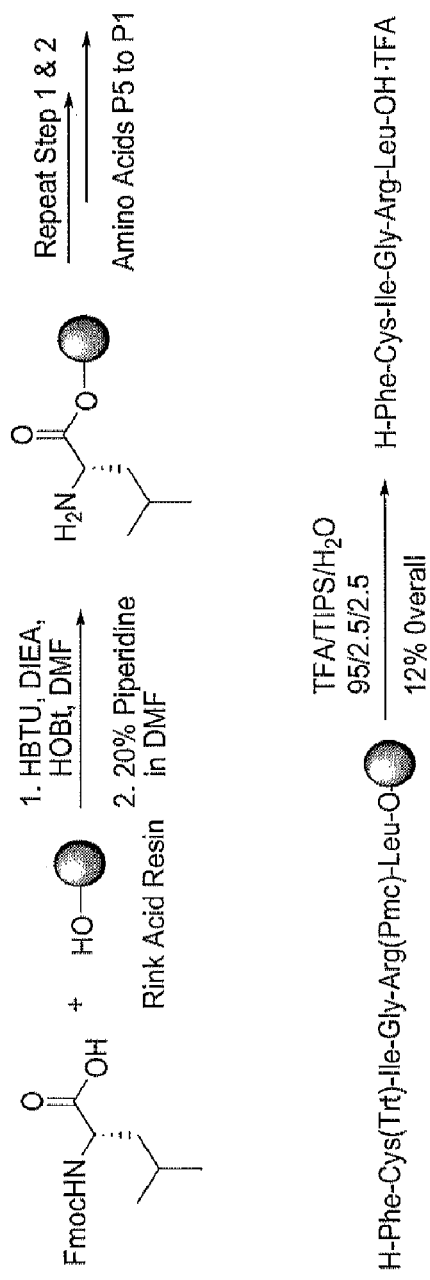
FIG. 1 is a schematic showing the steps involved in solid phase synthesis of an exemplary tight junction agonist of the invention.

As used herein, a "tight junction agonist" is a compound that mediates or induces or facilitates or augments the physiological, transient opening of tight junctions, for example, the tight junctions between adjacent epithelial cells. An example of a tight junction agonist is zonula occludens toxin (ZOT), which is produced by *Vibrio cholerae*. A ZOT receptor agonist is a compound which is believed to mediate tight junction opening through the same receptor utilized by ZOT. In some embodiments, a tight junction agonist may comprise a peptide.

As used herein a subject is any animal, e.g., mammal, upon which methods of the invention may be practiced and/or to which materials of the present invention may be administered. Subjects include, but are not limited to, humans.

Tight junction agonists of the invention may comprise peptide tight junction agonists. An exemplary peptide tight junction agonist is a peptide that comprises the amino acid sequence Phe Cys Ile Gly Arg Leu (SEQ ID NO:1). Additional examples of peptide tight junction agonists of the invention include, but are not limited to, peptides wherein one or more amino acids of SEQ ID NO:1 have been substituted with a different amino acid.

In certain embodiments, position 2 of SEQ ID NO:1 will be substituted. In preferred embodiments the Cysteine (Cys or C) residue at position 2 of SEQ ID NO:1 is replaced by an AllylGly residue. In such preferred embodiments the peptide tight junction agonist of the invention comprises the amino acids sequence Phe-AllylGly-Ile-Gly-Arg-Leu of SEQ ID NO:2. In some embodiments, more than one position of SEQ ID NO:2 will be substituted. Substitutions may be made at any of position(s) 1, 3, 4, 5 or 6 of SEQ ID NO:2. In some embodiments, substitutions are made at position 1 of SEQ ID NO:2. In some embodiments, substitutions are made at position 3 of SEQ ID NO:2. In some embodiments, substitutions are made at position 4 of SEQ ID NO:2. In some embodiments, substitutions are made at position 5 of SEQ ID NO:2. In some embodiments, substitutions are made at position 6 of SEQ ID NO:2. In some embodiments, additional substitutions may be made at positions 1, 3, 4, 5 and 6 of SEQ ID NO:2 In some embodiments, position 1 of SEQ ID NO:2 will be substituted with another naturally occurring amino acid. In some embodiments, position 1 of SEQ ID NO:2 will be substituted with a non-naturally occurring amino acid. In some embodiments, position 3 of SEQ ID NO:2 will be substituted with another naturally occurring amino acid. In some embodiments, position 3 of SEQ ID NO:2 will be substituted with a non-naturally occurring amino acid. In some embodiments, position 4 of SEQ ID NO:2 will be substituted with another naturally occurring amino acid. In some embodiments, position 4 of SEQ ID NO:2 will be substituted with a non-naturally occurring amino acid (e.g., non-genetically encoded). In some embodiments, position 5 of SEQ ID NO:2 will be substituted with another naturally occurring amino acid. In some embodiments, position 5 of SEQ ID NO:2 will be substituted with a non-naturally occurring amino acid. In some embodiments, position 6 of SEQ ID NO:2 will be substituted with another naturally occurring amino acid. In some embodiments, position 6 of SEQ ID NO:2 will be substituted with a non-naturally occurring amino acid. Non-naturally occurring amino acids of the present invention are listed in Table 7. In some embodiments, a peptide tight junction agonist may comprise one or more D-amino acids.

When the tight junction agonist is a peptide, any length of peptide may be used. Generally, the size of the peptide tight junction agonist will range from about 3 to about 100, from about 3 to about 90, from about 3 to about 80, from about 3 to about 70, from about 3 to about 60, from about 3 to about 50, from about 3 to about 40, from about 3 to about 30, from about 3 to about 25, from about 3 to about 20, from about 3 to about 15, from about 3 to about 10, from about 3 to about 9, from about 3 to about 8, from about 3 to about 7, from about 3 to about 6, from about 3 to about 5, or from about 3 to about 4 amino acids in length. As used herein, "about" used to modify a numerical value means within about 10% of the value. Peptide tight junction agonists of the invention may be about 3, 4, 5, 6, 7, 8, 9, 10 or more amino acids in length.

The peptide tight junction agonists can be chemically synthesized and purified using well-known techniques, such as described in *High Performance Liquid Chromatography of Peptides and Proteins: Separation Analysis and Conformation*, Eds. Mant et al., C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques. A schematic representation of a solid phase synthesis of an exemplary tight junction agonist of the invention is shown in FIG. 1.

As used herein, the term "peptide" includes molecules with conventional peptide backbones as well as peptidomimetics having modified backbones. Such modifications include, but are not limited to, cyclization, N-terminus modification and C-terminus modification (including addition or modification with a basic group such as an amine), peptide bond modification, including, but not limited to backbones containing $CH_2$—NH, $CH_2$—S, $CH_2$—S—O, O=C—NH, $CH_2$—O, $CH_2$—$CH_2$, S=C—NH, CH=CH or CF=CH. Methods for preparing peptidomimetic compounds are well known in the art and are specified in Quantitative Drug Design, C. A. Ramsden Gd., Chapter 17.2, F. Choplin Pergamon Press (1992), which is hereby incorporated by reference.

Compositions

Typically, compositions, such as pharmaceutical compositions, comprise a peptide tight junction agonist and optionally one or more additional active agents. Peptide tight junction agonists may be present in an amount sufficient to facilitate the opening of tight junctions, for example, the tight junctions between adjacent epithelial cells; or in amount sufficient to modulate an immune response to an antigen; or in an amount sufficient to reduce inflammation, in a subject in need thereof. The amount of agonist (e.g., peptide tight junction agonist) employed in any given composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation.

Generally, a pharmaceutical composition of the invention will comprise an amount of peptide tight junction agonist in the range of about 1 µg to about 1 g, preferably about 1 mg to about 1000 mg, from about 10 mg to about 100 mg, from about 10 mg to about 50 mg, or from about 10 mg to about 25 mg of peptide tight junction agonist. As used herein, "about" used to modify a numerical value means within 10% of the value.

Compositions of the invention may comprise one or more peptide tight junction agonists at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt %, from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition. As used herein, "about" used to modify a numerical value means within 10% of the value. Compositions of the invention may comprise one or more peptide tight junction agonists at a level of about 0.1 wt %, about 0.2 wt %, about 0.3 wt %, about 0.4 wt %, about 0.5 wt %, about 0.6 wt %, about 0.7 wt %, about 0.8 wt %, or about 0.9 wt % based on the total weight of the composition.

Compositions of the invention may comprise one or more peptide tight junction agonists at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. As used herein, "about" used to modify a numerical value means within 10% of the value. Compositions of the invention may comprise one or more peptide tight junction agonists at a level of about 1 wt %, about 2 wt %, about 3 wt %, about 4 wt %, about 5 wt %, about 6 wt %, about 7 wt %, about 8 wt %, or about 9 wt % based on the total weight of the composition.

Compositions of the invention, for example, pharmaceutical compositions comprising one or more peptide tight junction agonists and one or more additional active agents, may be formulated for pulmonary delivery (e.g., may be pulmonary dosage forms). Typically such compositions may be provided as pharmaceutical aerosols, e.g., solution aerosols or powder aerosols. Those of skill in the art are aware of many different methods and devices for the formation of pharmaceutical aerosols, for example, those disclosed by Sciarra and Sciarra, *Aerosols*, in *Remington: The Science and Practice of Pharmacy*, 20th Ed., Chapter 50, Gennaro et al. Eds., Lippincott, Williams and Wilkins Publishing Co., (2000).

In one embodiment, the dosage forms are in the form of a powder aerosol (i.e, comprise particles). These are particularly suitable for use in inhalation delivery systems. Powders may comprise particles of any size suitable for administration to the lung.

Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. In one embodiment, a powder formulation may comprise lactose as a carrier.

Powder formulations may be contained in any container known to those in the art. Containers may be capsules of, for example, gelatin or plastic, or in blisters (e.g. of aluminum or plastic), for use in a dry powder inhalation device. In some embodiments, the total weight of the formulation in the container may be from about 5 mg to about 50 mg. In other embodiments, powder formulations may be contained in a reservoir in a multi-dose dry powder inhalation device adapted to deliver a suitable amount per actuation.

Powder formulations typically comprise small particles. Suitable particles can be prepared using any means known in the art, for example, by grinding in an airjet mill, ball mill or vibrator mill, sieving, microprecipitation, spray-drying, lyophilisation or controlled crystallisation. Typically, particles will be about 10 microns or less in diameter. Particles for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. As used herein, "about" used to modify a numerical value means within 10% of the value. In some embodiments, particles for use in the invention may be about 1 micron, about 2 microns, about 3 microns, about 4 microns, about 5 microns, about 6 microns, about 7 microns, about 8 microns, about 9 microns, or about 10 microns in diameter.

In one embodiment, the dosage forms are in the form of a solution aerosol (i.e., comprise droplets). Typically, droplets will be about 10 microns or less in diameter. Droplets for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. As used herein, "about" used to modify a numerical value means within 10% of the value. In some embodiments, particles and/or droplets for use in the invention may be about 1 micron, about 2 microns, about 3 microns, about 4 microns, about 5 microns, about 6 microns, about 7 microns, about 8 microns, about 9 microns, or about 10 microns in diameter.

The compositions of the invention may be formulated for enteric delivery, for example, may comprise one or more coatings including, for example, a delayed release coating containing one or more enteric agents. A delayed release coating is typically substantially stable in gastric fluid and substantially unstable (e.g., dissolves rapidly or is physically unstable) in intestinal fluid, thus providing for substantial release of the peptide tight junction agonist and/or active agent from the composition in the duodenum or the jejunum.

The term "stable in gastric fluid" refers to a composition that releases 30% or less by weight of the total peptide tight junction agonist and/or active agent in the composition in gastric fluid with a pH of 5 or less, or simulated gastric fluid with a pH of 5 or less, in approximately sixty minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Compositions of the of the invention may release from about 0% to about 30%, from about 0% to about 25%, from about 0% to about 20%, from about 0% to about 15%, from about 0% to about 10%, from about 5% to about 30%, from about 5% to about 25%, from about 5% to about 20%, from about 5% to about 15%, from about 5% to about 10% by weight of the total peptide tight junction agonist and/or active agent in the composition in gastric fluid with a pH of 5 or less, or simulated gastric fluid with a pH of 5 or less, in approximately sixty minutes. As used herein, "about" used to modify a numerical value means within 10% of the value. Compositions of the invention may release about 1%, about 2%, about 3%, about 4%, about 5%, about 6%, about 7%, about 8%, about 9%, or about 10% by weight of the total peptide tight junction agonist in the composition in gastric fluid with a pH of 5 or less, or simulated gastric fluid with a pH of 5 or less, in approximately sixty minutes.

The term "unstable in intestinal fluid" refers to a composition that releases 70% or more by weight of the total peptide tight junction agonist and/or active agent in the composition in intestinal fluid or simulated intestinal fluid in approximately sixty minutes. The term "unstable in near neutral to alkaline environments" refers to a composition that releases 70% or more by weight of the total amount of tight junction agonist and/or active agent in the composition in intestinal fluid with a pH of 5 or greater, or simulated intestinal fluid with a pH of 5 or greater, in approximately ninety minutes. For example, a composition that is unstable in near neutral or alkaline environments may release 70% or more by weight of a tight junction agonist and/or active agent in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, from about 10 minutes to about 90 minutes, from about 15 minutes to about 90 minutes, from about 20 minutes to about 90 minutes, from about 25 minutes to about 90 minutes, from about 30 minutes to about 90 minutes, from about 5 minutes to about 60 minutes, from about 10 minutes to about 60 minutes, from about 15 minutes to about 60 minutes, from about 20 minutes to about 60 minutes, from about 25 minutes to about 60 minutes, or from about 30 minutes to about 60 minutes. As used herein, "about" used to modify a numerical value means within 10% of the value.

Compositions of the invention may be formulated for transcutaneous delivery (e.g., may be transcutaneous dosage forms). Typically such compositions may be provided as topical solutions and/or gels. Those of skill in the art are aware of many different methods and devices for the formation of topical medications, for example, those disclosed by Block, *Medicated Topicals*, in *Remington: The Science and Practice of Pharmacy*, 20th Ed., Chapter 44, Gennaro et al. Eds., Lippincott, Williams and Wilkins Publishing Co., (2000).

Additional Active Agents

In addition to one or more peptide tight junction agonists, compositions of the invention may further comprise one or more additional active agents, e.g., therapeutic agents, immunogenic agents and/or imaging agents.

Additional therapeutic agents that can be used in the compositions of the invention include agents that act on any organ of the body, such as heart, brain, intestine, or kidneys. Suitable additional therapeutic agents include, but are not limited to, glucose metabolism agents (e.g., insulin), antibiotics, antineoplastics, antihypertensives, antiepileptics, central nervous system agents, anti-inflammatory agents and immune system suppressants.

Additional therapeutic agents that can be used in the compositions of the invention include immunosuppressive agents. Such immunosuppressants used in the method and composition of the invention can be any agent which tends to attenuate the activity of the humoral or cellular immune systems. In particular, in one aspect the invention comprises compositions wherein the immunosuppressant is selected from the group consisting of cyclosporin A, FK506, prednisone, methylprednisolone, cyclophosphamide, thalidomide, azathioprine, and daclizumab, physalin B, physalin F, physalin G, seco-steroids purified from *Physalis angulata* L., 15-deoxyspergualin (DSG, 15-dos), MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliooxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane (SKF 105685), paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea, and combinations thereof. In one more particular aspect, the immunosuppressant is cyclosporin A.

Furthermore, the additional therapeutic agent can be selected from the group consisting of a chemotherapeutic, a gene therapy vector, a growth factor, a contrast agent, an angiogenesis factor, a radionuclide, an anti-infection agent, an anti-tumor compound, a receptor-bound agent, a hormone, a steroid, a protein, a complexing agent, a polymer, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antihypertensive agent, an antimicrobial agent, an antibiotic, a glycoprotein IIb/IIIa inhibitor, an inhibitor of surface glycoprotein receptors, an antiplatelet agent, an antimitotic, a microtubule inhibitor, a retinoid, an antisecretory agent, an actin inhibitor, a remodeling inhibitor, an antisense nucleotide, an agent for molecular genetic intervention, an antimetabolite, an antiproliferative agent, an anti-cancer agent, a dexamethasone derivative, an anti-inflammatory steroid, a non-steroidal anti-inflammatory agent, an immunosuppressive agent, a PDGF antagonist, a growth hormone antagonist, a growth factor antibody, an anti-growth factor antibody, a growth factor antagonist, a dopamine agonist, a radiotherapeutic agent, an iodine-containing compound, a barium-containing compound, a heavy metal functioning as a radiopaque agent, a peptide, a protein, an enzyme, an extracellular matrix component, a cellular component, an angiotensin converting enzyme inhibitor, a 21-aminosteroid, a free radical scavenger, an iron chelator, an antioxidant, a sex hormone, an antipolymerase, an antiviral agent, an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents, gene therapy agents, a prodrug, a photodynamic therapy agent, and an agent for treating benign prostatic hyperplasia (BHP), a $^{14}$C-, $^{3}$H-, $^{131}$I-, $^{32}$P- or $^{36}$S-radiolabelled form or other radiolabelled form of any of the foregoing, and combinations thereof.

More particularly, the additional therapeutic agent can be selected from the group consisting of parathyroid hormone, heparin, human growth hormone, covalent heparin, hirudin, hirulog, argatroban, D-phenylalanyl-L-poly-L-arginyl chloromethyl ketone, urokinase, streptokinase, nitric oxide, triclopidine, aspirin, colchicine, dimethyl sulfoxide, cytochalasin, deoxyribonucleic acid, methotrexate, tamoxifen citrate, dexamethasone, dexamethasone sodium phosphate, dexamethasone acetate, cyclosporin, trapidal, angiopeptin, angiogenin, dopamine, $^{60}$Co, $^{192}$Ir, $^{32}$P, $^{111}$In, $^{90}$Y, $^{99m}$Tc, pergolide mesylate, bromocriptine mesylate, gold, tantalum, platinum, tungsten, captopril, enalapril, ascorbic acid, α-tocopherol, superoxide dismutase, deferoxamine, estrogen, azidothymidine (AZT), acyclovir, famciclovir, rimantadine hydrochloride, ganciclovir sodium, 5-aminolevulinic acid, meta-tetrahydroxyphenylchlorin, hexadecafluoro zinc phthalocyanine, tetramethyl hematoporphyrin, and rhodamine 123, and combinations thereof.

Compositions of the invention may comprise one or more immunogenic agents, for example, antigens. Examples of antigens that can be used in the compositions of the invention (e.g., immunogenic and/or vaccine compositions) include peptides, proteins, microorganisms (e.g., attenuated and/or recombinant microorganisms), cells (e.g., cancer cells and/or recombinant cells) and viruses (e.g., attenuated and/or recombinant viruses). Examples of peptide antigens include the B subunit of the heat-labile enterotoxin of enterotoxigenic *E. coli*, the B subunit of cholera toxin, capsular antigens of enteric pathogens, fimbriae or pili of enteric pathogens, HIV surface antigens, cancer antigens (e.g., cancer cells comprising antigens, isolated antigens, etc.), dust allergens, and acari allergens. Other immunogenic compounds as are known in the art can also be used.

Examples of attenuated microorganisms and viruses that can be used in the compositions of the invention (e.g., vaccine compositions) include those of enterotoxigenic *Escherichia coli*, enteropathogenic *Escherichia coli*, *Vibrio cholerae*, *Shigella flexneri*, *Salmonella typhi* and rotavirus (Fasano et al, In: Le Vaccinazioni in Pediatria, Eds. Vierucci et al, CSH, Milan, pages 109-121 (1991); Guandalini et al, In: Management of Digestive and Liver Disorders in Infants and Children, Elsevior, Eds. Butz et al, Amsterdam, Chapter 25 (1993); Levine et al, Sem. Ped. Infect. Dis., 5.243-250 (1994); and Kaper et al, Clin. Micrbiol. Rev., 8:48-86 (1995), each of which is incorporated by reference herein in its entirety).

Any antigen capable of inducing a protective immune response may be used in the vaccine compositions of the invention. Examples of suitable antigens include, but are not limited to, measles virus antigens, mumps virus antigens, rubella virus antigens, *Corynebacterium diphtheriae* antigens, *Bordetella pertussis* antigens, *Clostridium tetani* antigens, *Bacillus anthracis* antigens, *Haemophilus influenzae* antigens, smallpox virus antigens, and influenza virus antigens.

Compositions of the invention may further comprise one or more protease inhibitors. Any protease inhibitor can be used, including, but not limited to, a proteinase, peptidase, endopeptidase, or exopeptidase inhibitor. A cocktail of inhibitors can also be used. Alternatively, the protease inhibitors can be selected from the group consisting of bestatin, L-trans-3-carboxyoxiran-2-carbonyl-L-leucylagmatine, ethylenediaminetetraacetic acid (EDTA), phenylmethylsulfonylfluoride (PMSF), aprotinin, amyloid protein precursor (APP), amyloid beta precursor protein, α1-proteinase inhibitor, collagen VI, bovine pancreatic trypsin inhibitor (BPTI), 4-(2-aminoethyl)-benzenesulfonyl fluoride (AEBSF), antipain, benzamidine, chymostatin, ε-aminocaproate, N-ethylmaleimide, leupeptin, pepstatin A, phosphoramidon, and combinations thereof. Novel protease inhibitors can also be used. Indeed, protease inhibitors can be specifically designed or selected to decrease the proteolysis of the tight junction agonist and/or the therapeutic agent.

Compositions of the invention may also comprise one or more pharmaceutically acceptable excipients. Suitable excipients include, but are not limited to, buffers, buffer salts, bulking agents, salts, surface active agents, acids, bases, sugars, binders, and the like.

Methods of Treatment

Peptide tight junction agonists and pharmaceutical compositions of the invention can be used for treating, ameliorating, and/or preventing a disease. Any disease may be treated using the compositions of the invention by selection of an appropriate active agent, e.g., therapeutic and/or immunogenic agent. In one embodiment, the present invention provides a method of treating diabetes response in a subject (e.g., a mammal such as a human) by administering a composition comprising one or more peptide tight junction agonists together with one or more insulins and/or derivatives thereof. In another embodiment, the invention provides a method of suppressing an excessive or undesirable immune response in a subject (e.g., a mammal such as a human) by administering a composition comprising one or more peptide tight junction agonists together with one or more immune-suppressive drugs that may include, for example, cyclosporin A.

Examples of diseases that can be treated using the compositions of the invention include, but are not limited to, cancer, autoimmune diseases, vascular disease, bacterial infections, gastritis, gastric cancer, collagenous colitis, inflammatory bowel disease, osteoporosis, systemic lupus erythematosus, food allergy, asthma, and irritable bowel syndrome. For example, to treat inflammatory bowel disease, a composition comprising one or more peptide tight junction agonists may be administered to the subject (e.g., a mammal such as a human) in need thereof.

In another example, to treat cancer of the colon or rectal area, a composition comprising a therapeutically effective amount of Erbitux® (Cetuximab) together with an absorption enhancing amount of one or more peptide tight junction agonists may be administered to the subject (e.g., a mammal such as a human) in need thereof. In another example, to treat breast cancer, a composition comprising a therapeutically effective amount of Herceptin® (Trastuzumab) together with an absorption enhancing amount of one or more peptide tight junction agonists may be administered to the subject (e.g., a mammal such as a human) in need thereof. In another example, to treat various types of cancer, a composition comprising a therapeutically effective amount of Avastin® (Bevacizumab) together with an absorption enhancing amount of one or more peptide tight junction agonists may be administered to the subject (e.g., a mammal such as a human) in need thereof. Another example involves treatment of osteoporosis by administration of a composition comprising one or more peptide tight junction agonists together with a therapeutically effective amount of Fosamax® (Alendronate) to the subject in need thereof. Another example involves treatment of transplant rejection by administration of a composition comprising one or more peptide tight junction agonists together with a therapeutically effective amount of Cyclosporin A to the subject in need thereof. Another example involves treatment of anemia by administration of a composition comprising one or more peptide tight junction agonists together with a therapeutically effective amount of erythropoietin to the subject in need thereof. Another example involves treatment of hemophilia by administration of a composition comprising one or more peptide tight junction agonists together with a therapeutically effective amount of Factor VIII to the subject in need thereof.

In some embodiments, compositions of the invention (e.g., pharmaceutical compositions) may be given repeatedly over a protracted period, i.e., may be chronically administered. Typically, compositions may be administered one or more times each day in an amount suitable to prevent, reduce the likelihood of an attack of, or reduce the severity of an attack of the underlying disease condition (e.g., diabetes, cancer, transplant rejection, etc). Such compositions may be administered chronically, for example, one or more times daily over a plurality of days.

In some embodiments, compositions of the invention (e.g., pharmaceutical compositions) may be used to treat acute attacks of the underlying disease (e.g., diabetes, cancer, transplant rejection, etc). Typically, embodiments of this type will require administration of the compositions of the invention to a subject undergoing an attack in an amount suitable to reduce the severity of the attack. One or more administrations may be used.

In some embodiments, peptide tight junction agonists of the invention may be used in the manufacture of compositions and pharmaceutical compositions for use in the methods described above.

The following examples are provided for illustrative purposes only, and are in no way intended to limit the scope of the present invention.

EXAMPLES

Example 1

Figure 7:
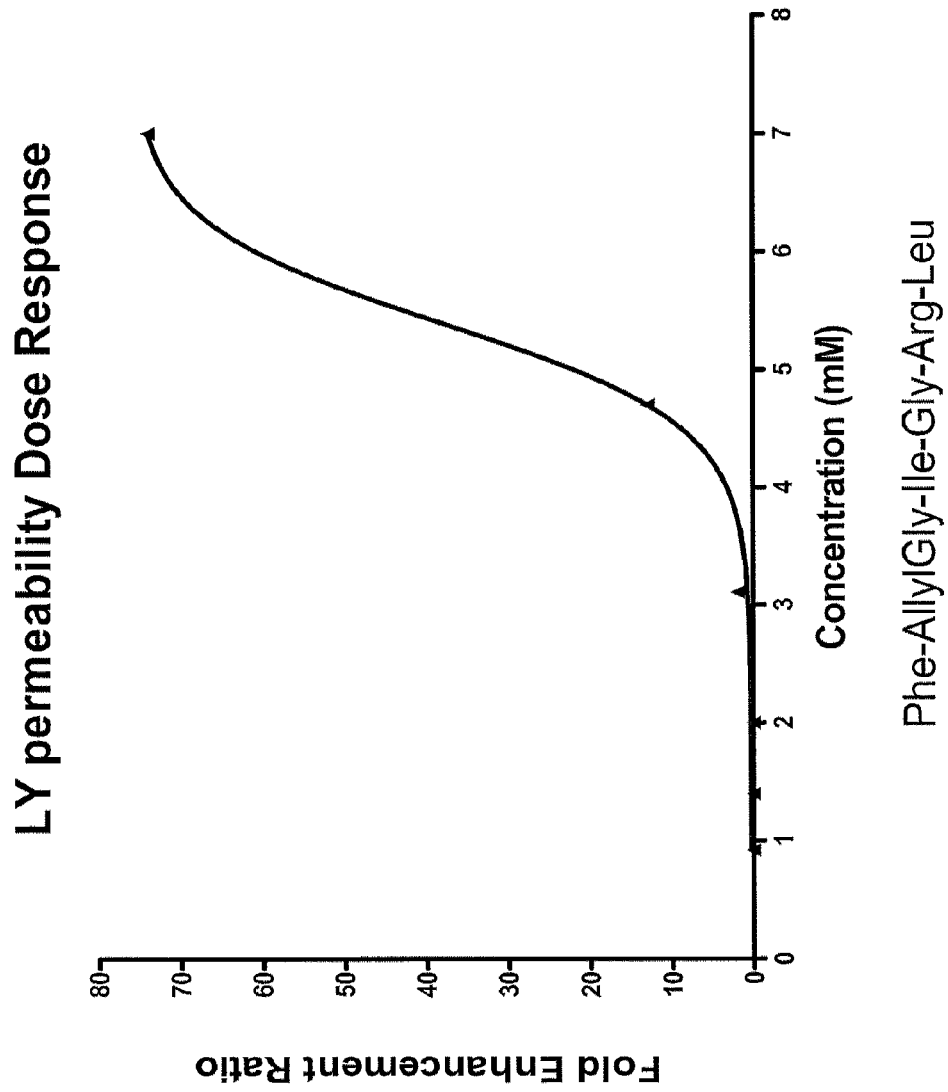
FIG. 7 is a dose response curve for the tight junction agonist of SEQ ID NO:2 in a Lucifer Yellow (LY) permeability assay as described in Example 1.
Figure 8:
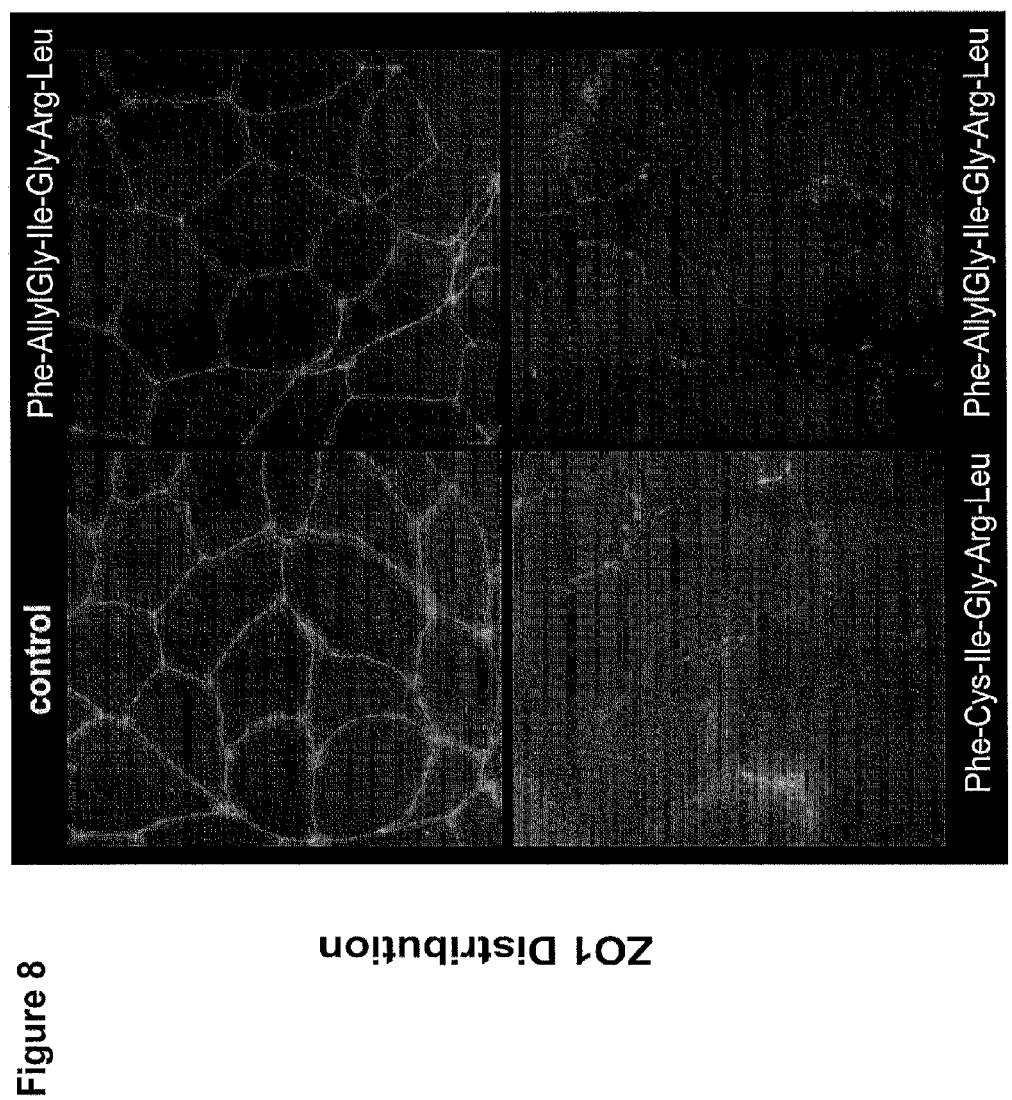
FIG. 8 is a fluorescence microscopy analysis comparing the effects of tight junction agonist FCIGRL (SEQ ID NO:1) and F-(Allyl)GIGRL (SEQ ID NO:2) on CaCo-2 cells grown in monolayer and stained for tight junction protein ZO-1. Cells were grown 21 days in a 6 well filter and treated with the junction agonist (apical and basolateral) for 3 hours.
Figure 9:
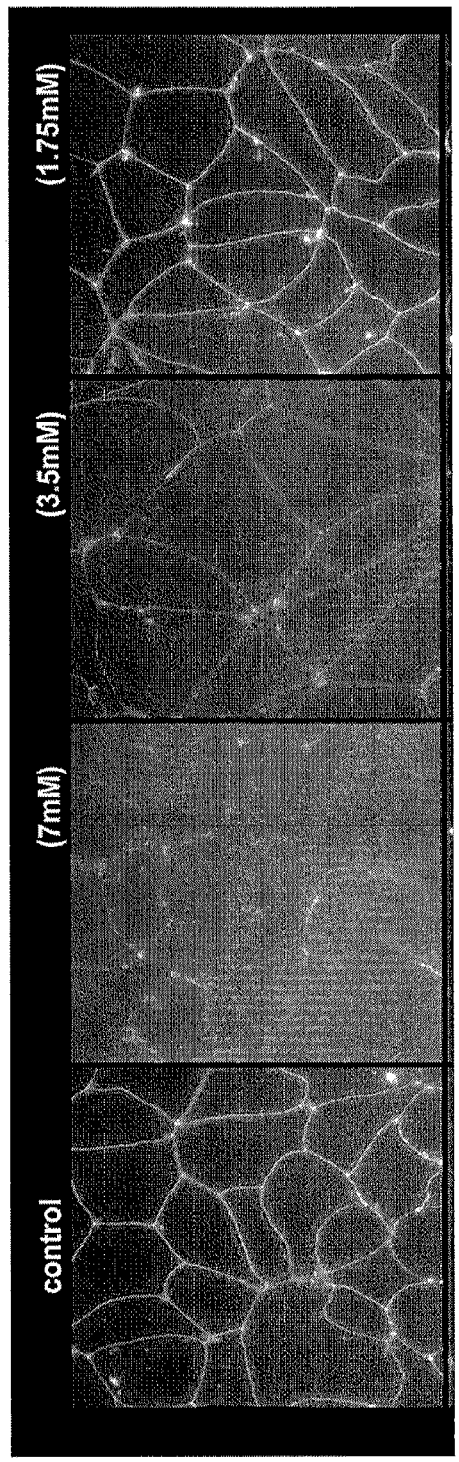
FIG. 9 is a fluorescence microscopy analysis showing a dose response of F-(Allyl)GIGRL (SEQ ID NO:2) on redistribution of ZO-1 in CaCo-2 BBE (Brush Border Expressing) cells grown in monolayer.
Figure 10:
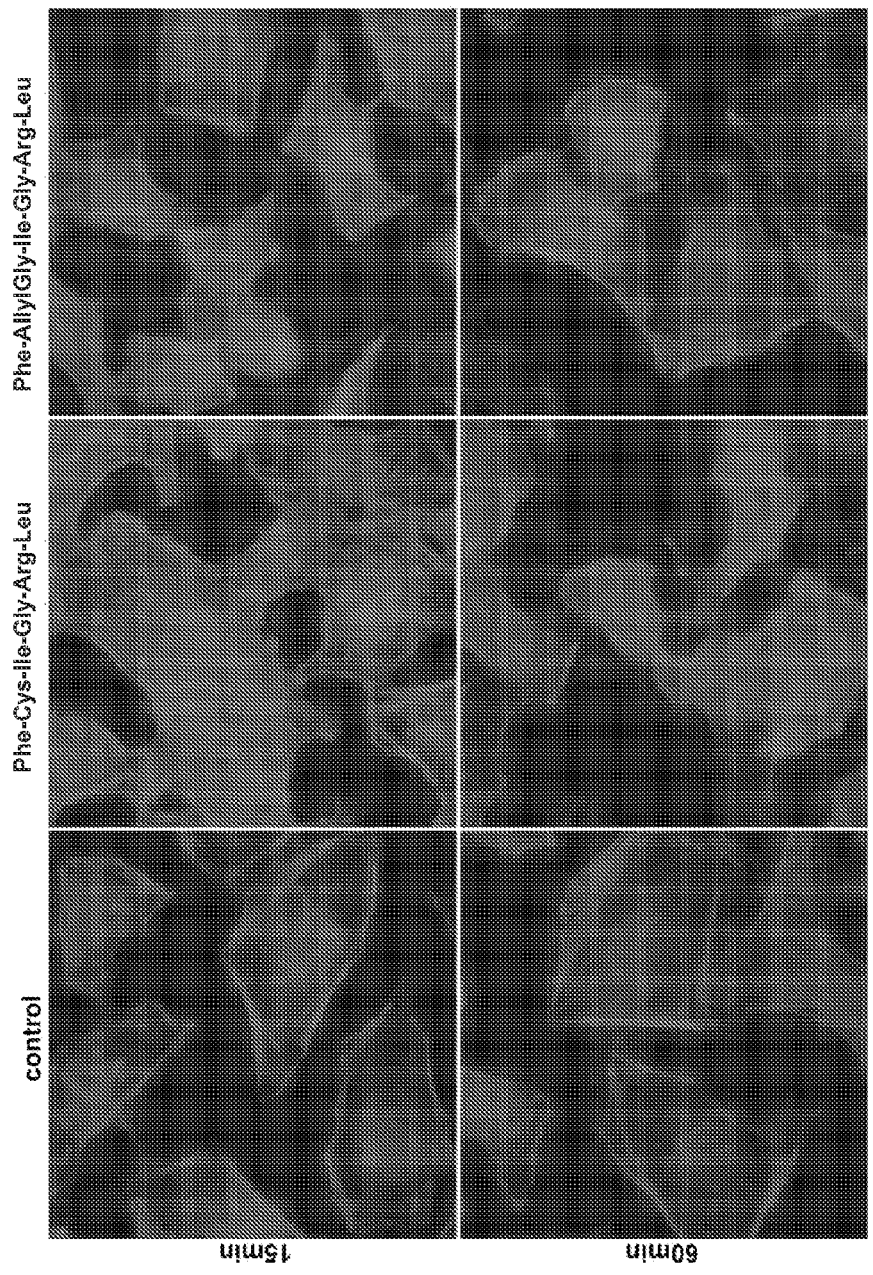
FIG. 10 is a fluorescence microscopy analysis showing the effects of FCIGRL (SEQ ID NO:1) and F-(Allyl)GIGRL (SEQ ID NO:2) on actin rearrangement in HeLa cells after 15 minutes and 60 minutes.

Measurement of Trans Epithelial Electric Resistance (TEER) and Epithelial Flux of a Fluorescent Marker Lucifer Yellow CaCo2 cells form monolayers that exhibit tight junctions between adjacent cells. Agonists of tight junctions can be identified by their ability to enhance the flux of compounds (e.g. ions, Lucifer Yellow) through a cell monolayer that comprises tight junctions; or by their ability to reduce TEER across a cell monolayer that comprises tight junctions. Treatment of CaCo2 monolayers with peptide FCIGRL (SEQ ID NO: 1) led to a 51-fold enhancement of Lucifer Yellow permeability through CaCo2 monolayers compared to vehicle alone. Further, FIG. 7 shows a dose response curve for the tight junction agonist of SEQ ID NO:2 in the Lucifer Yellow (LY) permeability assay.

Treatment of CaCo2 monolayers with peptide FCIGRL led to a 16-fold decrease in TEER across CaCo2 monolayers compared to vehicle alone.

Tight junction agonists can be identified and tested using the following method:

Determination of TEER and Lucifer Yellow flux

Prepare Modified Hank's Balanced Salt Solution (MH-BSS) by obtaining 1 L bottle of HBSS removing 10 ml of HBSS and replacing it with 10 ml HEPES buffer pH 7.0. Adjust pH to 7.4±0.1 using concentrated NaOH (10N).

Remove CaCo-2 cells from incubator, grown on 12-well, 3.0 µM, polycarbonate Transwell® filters (Corning) and record passage#, date cells seeded and age in days.

Aspirate cell culture medium from both the apical (AP) and basolateral (BL) compartments, replacing with 0.5 ml and 1.5 ml of MHBSS, respectively. Incubate cells at 37° C. for 30 minutes.

Using the MilliCell®-ERS instrument (Millipore), measure and record the transepithelial electrical resistance (TEER) across each filter and record.

Aspirate solution from the apical compartment of each filter (n=3 per condition) and replace with 0.5 ml of control and test solutions containing Lucifer Yellow and test compound If appropriate.

Place all plates into incubator set at 37° C. (±0.2), 50 RPM (±5) for a total of 180 minutes.

At t=30, 60, 120 and 180 minutes, measure and record the transepithelial electrical resistance (TEER) across each filter using the MilliCell-ERS instrument.

At t=60, 120 and 180 minutes remove 1000 from each basolateral compartment and place it in a 96-well plate for Lucifer Yellow analysis, replace with 100 µl of MHBSS.

Make a Lucifer Yellow standard curve with the following dilutions (7500 µM, 3750 µM, 750 µM, 375 µM, 75 µM, 37.5 µM, 7.5 µM, 3.75 µM, 0.75 µM) and pipette 100 µL of each into a 96-well plate except for the first three standards mentioned above which require a 1:10 dilutions prior to transferring to the 96-well plate.

Harvest the remaining start solutions and what is left in each apical compartment into 1.5 ml vials. Freeze at −20° C. for future analysis.

Analyze each 96-well plate in a Tecan Spectra Fluor Plus using Magellan at 485 and 535 nm.

Materials:

Cells: CaCo-2 cells passage 40-60 grown on Transwell plates for 21-28 days

Culture Medium: DMEM supplemented with 10% fetal bovine serum, 1% NEAA, 1% Penn/Strep Buffers: Hank's Balanced Salt Solution (HBSS) without calcium and magnesium Flasks: 100×20 mm Tissue culture dish Falcon.

Plates: 12 well polycarbonate Transwell filters; 0.3 uM pore size

Example 2

Identification of Tight Junction Agonists Using Real-Time Cell Electronic Sensing (RT-CES)

IEC6 cells form monolayers that exhibit tight junctions between adjacent cells. Agonists of tight junctions can be identified by their ability to induce changes in morphology of cells in a monolayer of cells that comprise tight junctions. Such changes in the morphology of IEC6 cells may be measured using a Real-Time Cell Electronic Sensing protocol as described below.

Tight junction agonists can be identified using the following method:

Materials: cells: IEC6 passage 30-50, medium: DMEM 10% no calcium no magnesium, foetal bovine serum 0.1 unit per ml bovine insulin, buffers: phosphate buffered saline (PBS) no calcium no magnesium, trypsin: 0.25% porcine trypsin in HBSS no calcium no magnesium, flasks: 100×20 mm Tissue culture dish Falcon, plates: 16× E-Plate, machine: RT-CES™ 16× system (ACEA Biosciences, Inc., San Diego, Calif.)

Wash a 75 cm$^2$ flask of confluent IEC6 cells twice with 25 ml of PBS.

Add 2.5 ml of trypsin to the flask and place back in the incubator at 37° C.

Wash cells from the surface of the flask with 10 ml of serum containing media to quench the trypsin.

Pellet the cells by centrifugation at 1500 rpm for 5 minutes aspirate the media.

Resuspend the cell pellet in 10 ml of serum free media and centrifuge at 1500 rpm for 5 minutes aspirate the media and repeat for a total of 5 washes.

Take 100 µl of cells and mix with 100 µl of trypan blue.

Count the cells four times and use the average cell concentration.

Dilute the cells to $1 \times 10^6$ per ml in serum free media.

Add 100 µl of serum free media to each well of the ACEA plates to be used.

Insert the ACEA plate and press scan.

Run step 1 of the program to measure background.

Add 50 µl of cells to each well of the ACEA plate tap each slide of the plate 10 times and place the cells on the bench for 15 minutes to allow the cells to settle.

Insert the ACEA plate and run the scan step to check connections and run step 2-1 and 2-2 overnight.

Step 2-1 sample every 2 minutes 30 times.

Step 2-2 sample every 15 minutes 100 times.

The cell indices should be between 6-10 after the overnight run and should have reached a plateau.

Remove 100 µl of media carefully from each well.

Make up the compounds to be tested so that 50 µl contains 2× the desired final concentration.

Add 50 µl of compounds to the designated wells.

Scan the plate to check connections.

Run steps 3-1 and 3-2.

Step 3-1 sample every 2 minutes 30 times.

Step 3-2 sample every 15 minutes 100 times.

Figure 2:
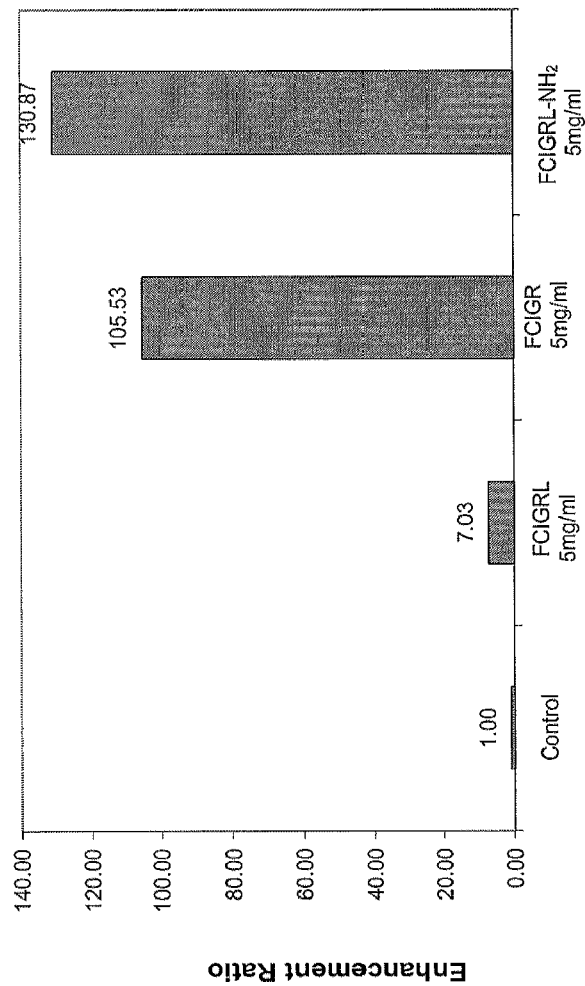
FIG. 2 is a bar graph showing the results of a Real-Time Cell Electronic Sensing assay comparing the activity of various compounds of the invention to known tight junction agonist peptide FCIGRL (SEQ ID NO: 1).
Figure 3:
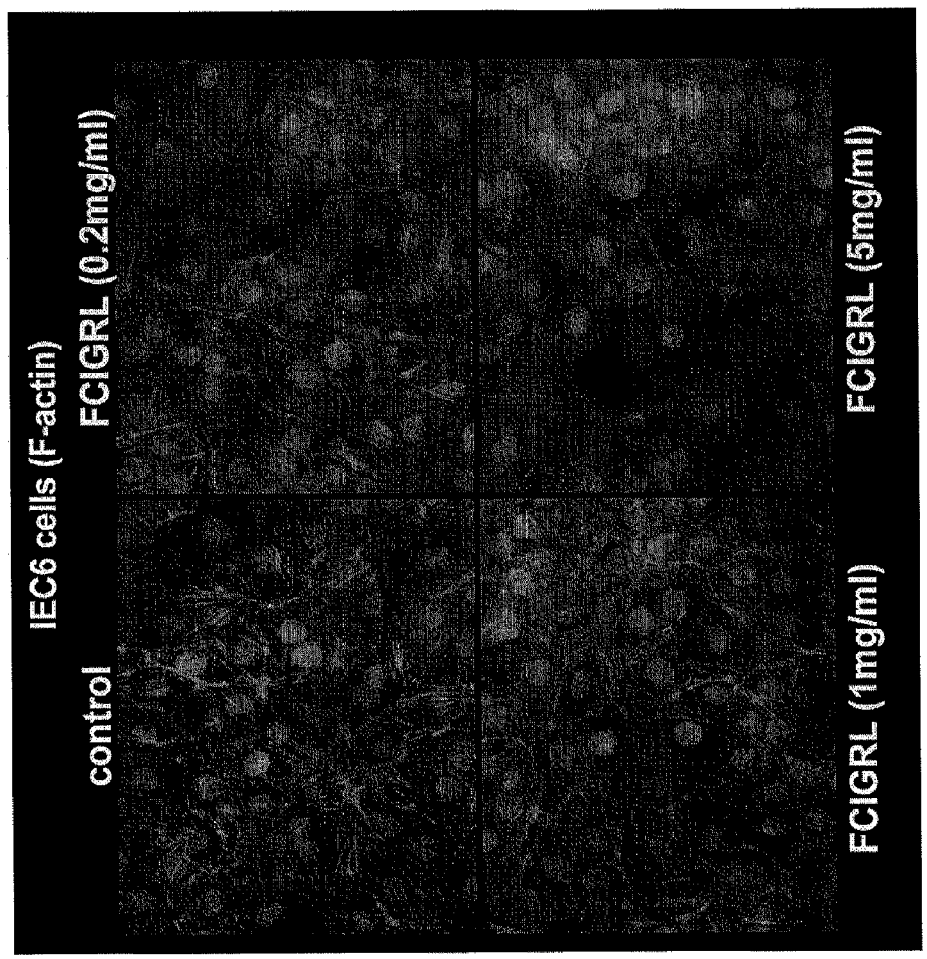
FIG. 3 is a fluorescence microscopy analysis of the effects of tight junction agonist FCIGRL (SEQ ID NO:1) on IEC6 cells grown in monolayer and stained for F-actin.
Figure 4:
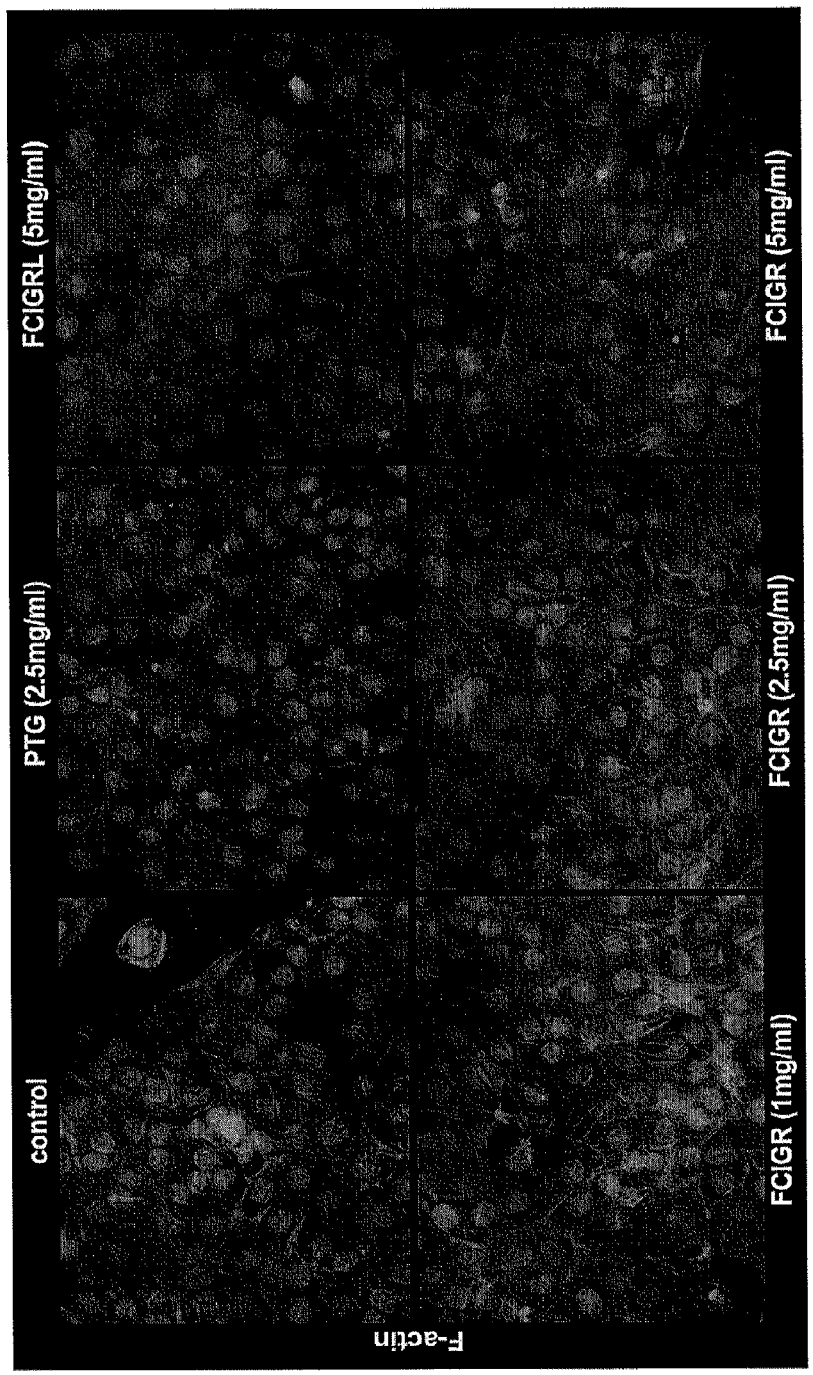
FIG. 4 is a fluorescence microscopy analysis of the effects of PT-gliadin, tight junction agonist FCIGRL (SEQ ID NO:1), and various doses of tight junction agonist FCIGR on IEC6 cells grown in monolayer and stained for F-actin.
Figure 5:
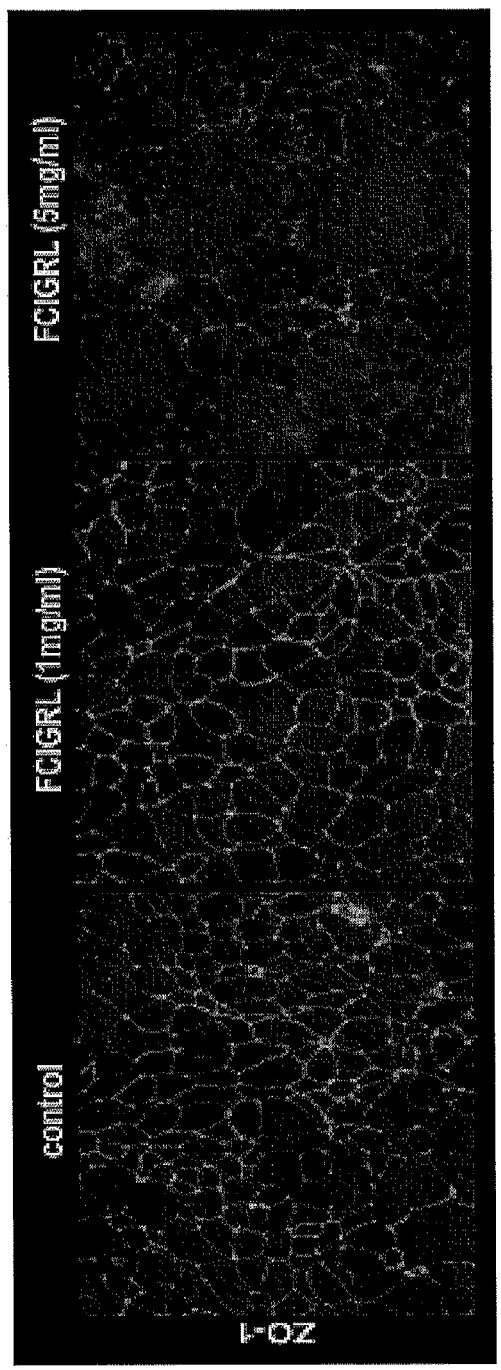
FIG. 5 is a fluorescence microscopy analysis of the effects of tight junction agonist FCIGRL (SEQ ID NO:1) on CaCo-2 cells grown in monolayer and stained for tight junction protein ZO-1. Cells were grown 21 days in a 6 well filter and treated with the junction agonist (apical and basolateral) for 3 hours.
Figure 6:
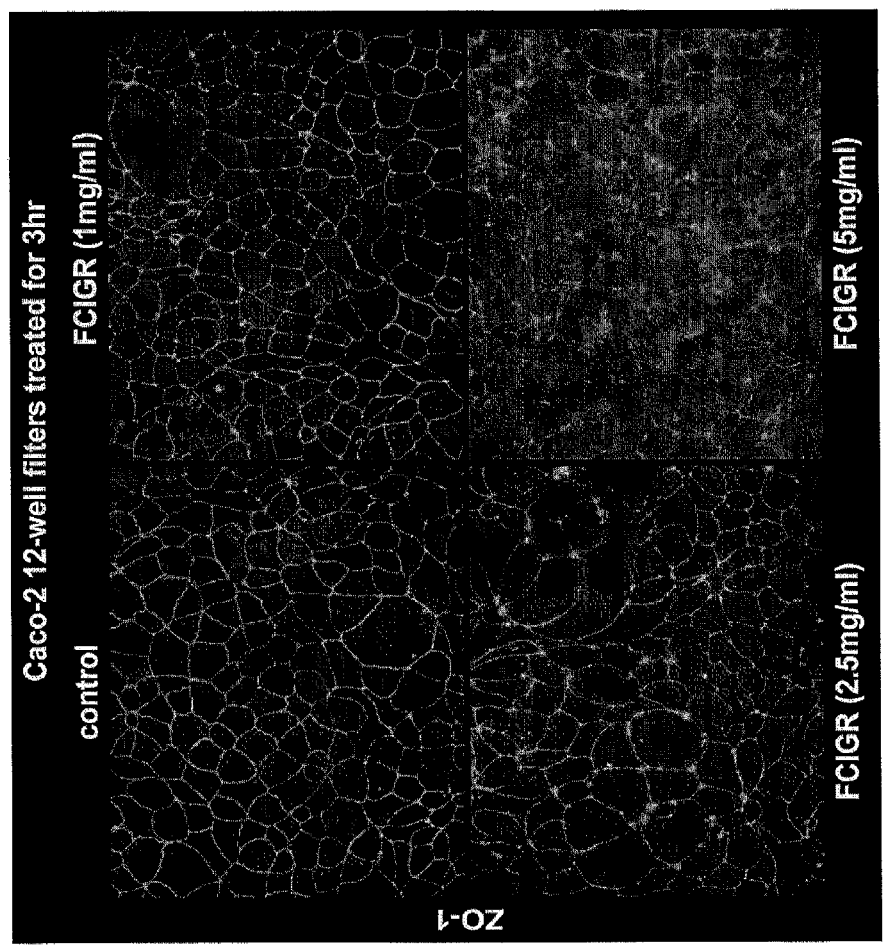
FIG. 6 is a fluorescence microscopy analysis of the effects of tight junction agonist FCIGR on CaCo-2 cells grown in monolayer and stained for tight junction protein ZO-1.

FIG. 2 shows a comparison of ACEA data for the indicated tight junction agonists.

Example 3

Assay of Cytoskeletal Rearrangement Induced by Tight Junction Agonists

Gliadin treated with the peptidases pepsin and trypsin (termed PT-gliadin or PTG) induces a cytoskeletal arrangement in CaCo2 cells grown in monolayers.

The rearrangement can be visualized using a Nikon-TE2000 epifluorescence microscope and a 40× objective and Alexa Fluor 555 conjugated phalloidin (Invitrogen, Carlsbad, Calif.), which binds specifically to F-actin. Exposure times were identical for control and agonist treated samples. The figures were generated using Adobe Photoshop CS2 v 9.0.2. The concentration of agonist was as indicated. Tight junction agonists can be identified by their ability to induce the cytoskeletal rearrangement as shown by the effects of peptide FCIGRL, a known tight junction agonist. FIGS. 3-6 and 8-11 show the cytoskeletal rearrangements induced by exemplary tight junction agonists of the invention, including with respect to the distribution of F-actin and the tight junction protein ZO-1.

Additional results are provided in the following tables. The first column of the table provides SEQ ID NO: of the peptide, the second column provides the sequence of the peptides tested, the third column provides the results of the indicated assay (i.e., ACEA, TEER reduction, or Lucifer Yellow flux).

In the following tables + indicates an enhancement of the permeability of the tight junctions were observed and – indicates no enhancement of permeability was observed.

TABLE 1

Amino acid substitutions at position 2 of SEQ ID NO: 1.

| SEQ ID NO: | Sequence | Enhanced LY permeability | Reduced TEER |
|---|---|---|---|
| 1 | Phe-Cys-Ile-Gly-Arg-Leu | + | + |
| 2 | Phe-AllylGly-Ile-Gly-Arg-Leu-OH | + | + |
| 3 | Phe-AllylGly-Ile-Gly-Arg-NH2 | – | – |
| 4 | Phe-(d)AllylGly-Ile-Gly-Arg-NH2 | – | – |

TABLE 2

Amino acid substitutions at position 1 of SEQ ID NO: 2.

| SEQ ID NO: | Sequence | Enhanced LY permeability | Reduced TEER |
|---|---|---|---|
| 1 | Phe-Cys-Ile-Gly-Arg-Leu | + | + |
| 5 | Met-AllylGly-Ile-Gly-Arg-Leu-NH2 | + | – |
| 6 | Gln-AllylGly-Ile-Gly-Arg-Leu-NH2 | – | – |
| 7 | Leu-AllylGly-Ile-Gly-Arg-Leu-NH2 | + | – |
| 8 | Ser-AllylGly-Ile-Gly-Arg-Leu-NH2 | – | – |
| 9 | Thr-AllylGly-Ile-Gly-Arg-Leu-NH2 | – | – |
| 10 | Glu-AllylGly-Ile-Gly-Arg-Leu-NH2 | – | – |
| 11 | Val-AllylGly-Ile-Gly-Arg-Leu-NH2 | – | – |
| 12 | Tyr-AllylGly-Ile-Gly-Arg-Leu-NH2 | – | – |
| 13 | Gly-AllylGly-Ile-Gly-Arg-Leu-NH2 | – | – |
| 14 | Asp-AllylGly-Ile-Gly-Arg-Leu-NH2 | – | – |
| 15 | Trp-AllylGly-Ile-Gly-Arg-Leu-NH2 | + | – |
| 16 | Lys-AllylGly-Ile-Gly-Arg-Leu-NH2 | – | – |
| 17 | Ala-AllylGly-Ile-Gly-Arg-Leu-NH2 | – | – |
| 18 | His-AllylGly-Ile-Gly-Arg-Leu-NH2 | – | – |
| 19 | Pro-AllylGly-Ile-Gly-Arg-Leu-NH2 | – | – |
| 20 | Arg-AllylGly-Ile-Gly-Arg-Leu-NH2 | + | – |
| 21 | Ile-AllylGly-Ile-Gly-Arg-Leu-NH2 | – | – |

TABLE 3

Amino acid substitutions at position 3 of SEQ ID NO: 2.

| SEQ ID NO: | Sequence | Enhanced LY permeability | Reduced TEER |
|---|---|---|---|
| 1 | Phe-Cys-Ile-Gly-Arg-Leu | + | + |
| 22 | Phe-AllylGly-Pro-Gly-Arg-Leu-NH2 | – | – |
| 23 | Phe-AllylGly-Phe-Gly-Arg-Leu-NH2 | + | + |
| 24 | Phe-AllylGly-Thr-Gly-Arg-Leu-NH2 | – | – |
| 25 | Phe-AllylGly-Leu-Gly-Arg-Leu-NH2 | + | + |
| 26 | Phe-AllylGly-Ser-Gly-Arg-Leu-NH2 | + | + |
| 27 | Phe-AllylGly-Phe-Gly-Arg-Leu-NH2 | + | + |
| 28 | Phe-AllylGly-Val-Gly-Arg-Leu-NH2 | – | – |
| 29 | Phe-AllylGly-Gly-Gly-Arg-Leu-NH2 | + | + |
| 30 | Phe-AllylGly-Ala-Gly-Arg-Leu-NH2 | + | + |
| 31 | Phe-AllylGly-His-Gly-Arg-Leu-NH2 | + | + |
| 32 | Phe-AllylGly-Asp-Gly-Arg-Leu-NH2 | + | + |
| 33 | Phe-AllylGly-Glu-Gly-Arg-Leu-NH2 | + | + |
| 34 | Phe-AllylGly-Gln-Gly-Arg-Leu-NH2 | + | + |
| 35 | Phe-AllylGly-Arg-Gly-Arg-Leu-NH2 | + | + |
| 36 | Phe-AllylGly-Lys-Gly-Arg-Leu-NH2 | + | + |
| 37 | Phe-AllylGly-Asn-Gly-Arg-Leu-NH2 | + | + |
| 38 | Phe-AllylGly-Tyr-Gly-Arg-Leu-NH2 | + | + |

TABLE 4

Amino acid substitutions at position 4 of SEQ ID NO: 2.

| SEQ ID NO: | Sequence | Enhanced LY permeability | Reduced TEER |
|---|---|---|---|
| 1 | Phe-Cys-Ile-Gly-Arg-Leu | + | + |
| 39 | Phe-AllylGly-Ile-Thr-Arg-Leu-NH2 | + | + |
| 40 | Phe-AllylGly-Ile-Leu-Arg-Leu-NH2 | | |
| 41 | Phe-AllylGly-Ile-Ile-Arg-Leu-NH2 | | |
| 42 | Phe-AllylGly-Ile-Ala-Arg-Leu-NH2 | + | + |
| 43 | Phe-AllylGly-Ile-Pro-Arg-Leu-NH2 | – | – |
| 44 | Phe-AllylGly-Ile-Gly-Arg-Leu-NH2 | | |
| 45 | Phe-AllylGly-Ile-His-Arg-Leu-NH2 | + | + |
| 46 | Phe-AllylGly-Ile-Asp-Arg-Leu-NH2 | + | + |
| 47 | Phe-AllylGly-Ile-Glu-Arg-Leu-NH2 | + | + |
| 48 | Phe-AllylGly-Ile-Gln-Arg-Leu-NH2 | + | + |
| 49 | Phe-AllylGly-Ile-Phe-Arg-Leu-NH2 | + | + |
| 50 | Phe-AllylGly-Ile-Arg-Arg-Leu-NH2 | | |
| 51 | Phe-AllylGly-Ile-Lys-Arg-Leu-NH2 | – | – |
| 52 | Phe-AllylGly-Ile-Asn-Arg-Leu-NH2 | + | + |
| 53 | Phe-AllylGly-Ile-Ser-Arg-Leu-NH2 | + | + |
| 54 | Phe-AllylGly-Ile-Val-Arg-Leu-NH2 | – | + |

TABLE 5

Amino acid substitutions at position 5 of SEQ ID NO: 2.

| SEQ ID NO: | Sequence | Enhanced LY permeability | Reduced TEER |
|---|---|---|---|
| 1 | Phe-Cys-Ile-Gly-Arg-Leu | + | + |
| 55 | Phe-AllylGly-Ile-Gly-His-Leu-NH2 | – | – |
| 56 | Phe-AllylGly-Ile-Gly-Asp-Leu-NH2 | + | + |
| 57 | Phe-AllylGly-Ile-Gly-Glu-Leu-NH2 | – | – |
| 58 | Phe-AllylGly-Ile-Gly-Gln-Leu-NH2 | – | – |
| 59 | Phe-AllylGly-Ile-Gly-Gly-Leu-NH2 | + | + |
| 60 | Phe-AllylGly-Ile-Gly-Ala-Leu-NH2 | + | |
| 61 | Phe-AllylGly-Ile-Gly-Phe-Leu-NH2 | | |
| 62 | Phe-AllylGly-Ile-Gly-Lys-Leu-NH2 | + | + |
| 63 | Phe-AllylGly-Ile-Gly-Leu-Leu-NH2 | | |
| 64 | Phe-AllylGly-Ile-Gly-Met-Leu-NH2 | | |
| 65 | Phe-AllylGly-Ile-Gly-Asn-Leu-NH2 | | |
| 66 | Phe-AllylGly-Ile-Gly-Ser-Leu-NH2 | | |
| 67 | Phe-AllylGly-Ile-Gly-Tyr-Leu-NH2 | | |
| 68 | Phe-AllylGly-Ile-Gly-Thr-Leu-NH2 | | + |
| 69 | Phe-AllylGly-Ile-Gly-Ile-Leu-NH2 | | – |
| 70 | Phe-AllylGly-Ile-Gly-Trp-Leu-NH2 | + | + |
| 71 | Phe-AllylGly-Ile-Gly-Pro-Leu-NH2 | + | – |
| 72 | Phe-AllylGly-Ile-Gly-Val-Leu-NH2 | – | + |

TABLE 6

Amino acid substitutions at position 6 of SEQ ID NO: 2.

| SEQ ID NO: | Sequence | Enhanced LY permeability | Reduced TEER |
|---|---|---|---|
| 1 | Phe-Cys-Ile-Gly-Arg-Leu | + | + |
| 73 | Phe-AllylGly-Ile-Gly-Arg-His-NH2 | + | + |
| 74 | Phe-AllylGly-Ile-Gly-Arg-Asp-NH2 | + | + |

TABLE 6-continued

Amino acid substitutions at position 6 of SEQ ID NO: 2.

| SEQ ID NO: | Sequence | Enhanced LY permeability | Reduced TEER |
|---|---|---|---|
| 75 | Phe-AllylGly-Ile-Gly-Arg-Arg-NH2 | + | − |
| 76 | Phe-AllylGly-Ile-Gly-Arg-Phe-NH2 | + | + |
| 77 | Phe-AllylGly-Ile-Gly-Arg-Ala-NH2 | + | − |
| 78 | Phe-AllylGly-Ile-Gly-Arg-Gly-NH2 | + | − |
| 79 | Phe-AllylGly-Ile-Gly-Arg-Gln-NH2 | − | − |
| 80 | Phe-AllylGly-Ile-Gly-Arg-Glu-NH2 | + | + |
| 81 | Phe-AllylGly-Ile-Gly-Arg-Thr-NH2 | − | + |
| 82 | Phe-AllylGly-Ile-Gly-Arg-Tyr-NH2 | + | + |
| 83 | Phe-AllylGly-Ile-Gly-Arg-Ser-NH2 | − | − |
| 84 | Phe-AllylGly-Ile-Gly-Arg-Asn-NH2 | + | + |
| 85 | Phe-AllylGly-Ile-Gly-Arg-Met-NH2 | + | + |
| 86 | Phe-AllylGly-Ile-Gly-Arg-Lys-NH2 | + | − |
| 87 | Phe-AllylGly-Ile-Gly-Arg-Ile-NH2 | + | + |
| 88 | Phe-AllylGly-Ile-Gly-Arg-Trp-NH2 | + | + |
| 89 | Phe-AllylGly-Ile-Gly-Arg-Pro-NH2 | − | − |
| 90 | Phe-AllylGly-Ile-Gly-Arg-Val-NH2 | + | + |

TABLE 7

Abbreviations and Structures of Non-Naturally Occurring Amino Acids.

| Abbreviation | IUPAC Name | Chemical Structure |
|---|---|---|
| Sar | Sarcosine | 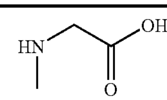 |
| Aib | alpha-aminoisobutyric acid | 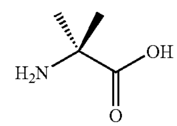 |
| Tle | L-tert-Leucine | 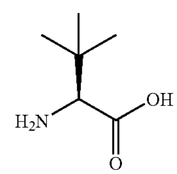 |
| MeAla | L-N-methyl Alanine | 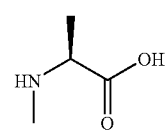 |
| Abu | L-alpha-aminobutyric acid | 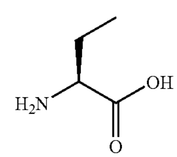 |
| Phe(4-NO2) | L-4-nitro-phenylalanine | 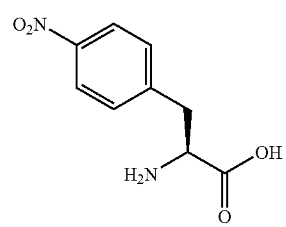 |
| Phe(4-Cl) | L-4-chlorophenylalanine | 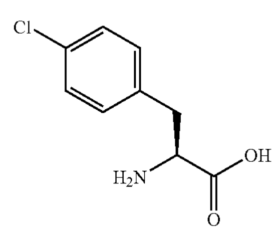 |

TABLE 7-continued

Abbreviations and Structures of Non-Naturally Occurring Amino Acids.

| Abbreviation | IUPAC Name | Chemical Structure |
|---|---|---|
| Tic | L-1,2,3,4-tetrahydroisoquinoline-3-carboxylic acid | 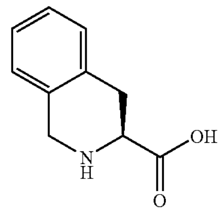 |
| Thi | L-beta-(2-thienyl)-alanine | 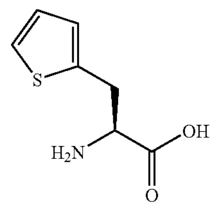 |
| Met(O) | L-methionine-sulfoxide | 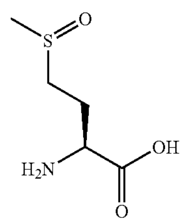 |
| Met(O)$_2$ | L-methionine-sulfone | 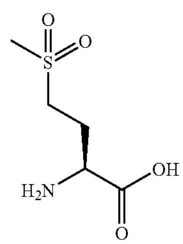 |
| Nle | L-norleucine | 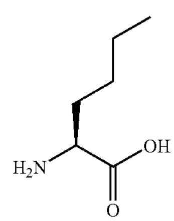 |
| Cys(S-benzyl) | L-S-benzyl-cysteine | 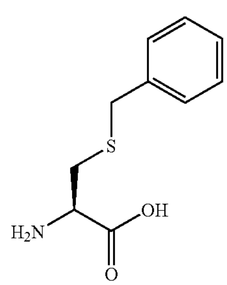 |

TABLE 7-continued
Abbreviations and Structures of Non-Naturally Occurring Amino Acids.
| Abbreviation | IUPAC Name | Chemical Structure |
|---|---|---|
| Cys(t-buthiol) | L-S-tert-butylthio-cysteine | 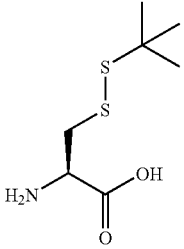 |
| Phg | L-phenylglycine | 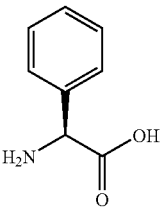 |
| Cha | L-beta-cyclohexyl-alanine | 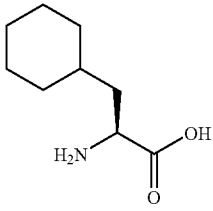 |
| (Allyl)Gly | L-allylglycine | 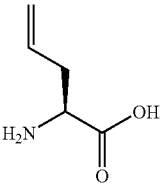 |
| (t-Bu)Gly | L-tert-butylglycine | 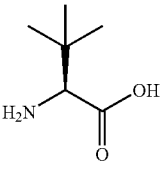 |
| Dab | L-1,4-diaminobutyric acid | 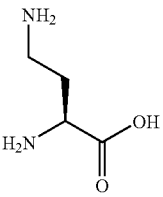 |
| (cyclopropane)Pro | L-(R,S)-3,4-cis-methanoproline | 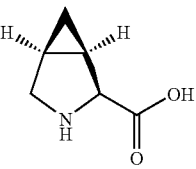 |

TABLE 7-continued

Abbreviations and Structures of Non-Naturally Occurring Amino Acids.

| Abbreviation | IUPAC Name | Chemical Structure |
|---|---|---|
| Dap/Dpr | L-1,3-diaminopropionic acid | 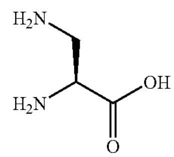 |
| Pen(Acm) | L-S-acetamidomethyl-penicillamine | 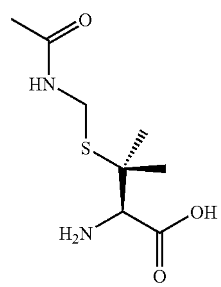 |
| (2-pyridyl)Ala | L-beta-(2-pyridyl)-alanine | 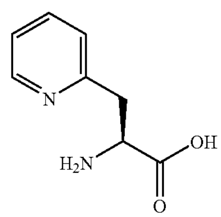 |
| (4,5-dehydro)Leu | L-4,5-dehydro-leucine | 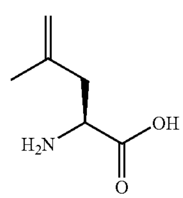 |
| Phe(4-CN) | L-4-cyano-phenylalanine | 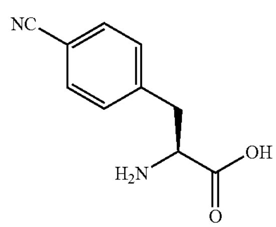 |
| Phe(3-Me) | L-3-methyl-phenylalanine | 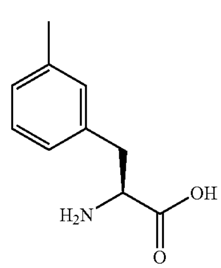 |

TABLE 7-continued

Abbreviations and Structures of Non-Naturally Occurring Amino Acids.

| Abbreviation | IUPAC Name | Chemical Structure |
| --- | --- | --- |
| (cyclopropyl)Ala | L-beta-cyclopropyl-alanine | 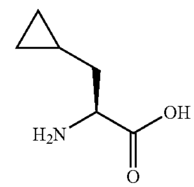 |
| Pra | L-propargylglycine | 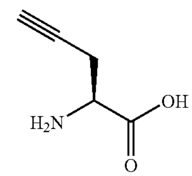 |
| (2-furyl)Ala | L-beta-(2-furyl)-alanine | 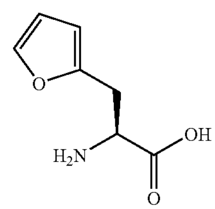 |
| Thh | 1,2,3,4-tetrahydroharmane-3-carboxylic acid | 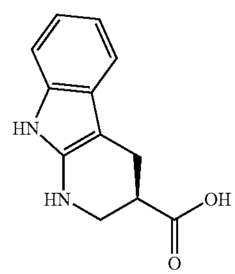 |
| (styryl)Gly | L-beta-styryl-alanine | 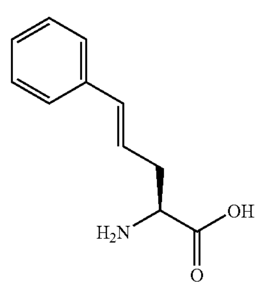 |
| HOCit | Homocitrulline | 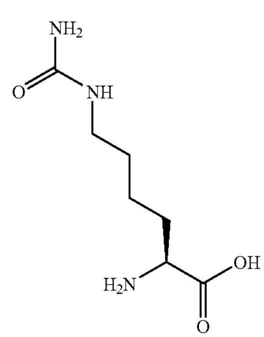 |

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A synthetic peptide tight junction agonist that comprises the amino acid sequence of SEQ ID NO: 2.

2. A pharmaceutical composition comprising the peptide tight junction agonist of claim 1 and at least one pharmaceutically acceptable excipient and at least one therapeutic or immunogenic agent.

3. The pharmaceutical composition of claim 2, wherein the composition is formulated for enteric delivery.

4. An isolated peptide consisting of the amino acid sequence of SEQ ID NO: 2.

5. A pharmaceutical composition comprising the peptide of claim 4 and at least one therapeutic or immunogenic agent.

6. The pharmaceutical composition of claim 5, wherein the composition is formulated for enteric delivery.

* * * * *